(12) United States Patent
Lee et al.

(10) Patent No.: US 12,022,711 B2
(45) Date of Patent: Jun. 25, 2024

(54) DISPLAY DEVICE

(71) Applicant: Samsung Display Co., Ltd., Yongin-Si (KR)

(72) Inventors: Hyeon Jun Lee, Hanam-si (KR); Gyeong Ub Moon, Suwon-si (KR); Chul Kim, Hwaseong-si (KR); Jong Yeop An, Hwaseong-si (KR); Bo Ram Choi, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 99 days.

(21) Appl. No.: 17/839,840

(22) Filed: Jun. 14, 2022

(65) Prior Publication Data

US 2023/0165096 A1 May 25, 2023

(30) Foreign Application Priority Data

Nov. 19, 2021 (KR) .................. 10-2021-0160608

(51) Int. Cl.
*G09G 5/00* (2006.01)
*A61B 5/00* (2006.01)
*A61B 5/021* (2006.01)
*G06F 3/01* (2006.01)
*H10K 59/35* (2023.01)
*H10K 59/65* (2023.01)
*G06F 1/16* (2006.01)

(52) U.S. Cl.
CPC ....... *H10K 59/351* (2023.02); *A61B 5/02108* (2013.01); *A61B 5/02141* (2013.01); *A61B 5/6898* (2013.01); *G06F 3/011* (2013.01); *H10K 59/65* (2023.02); *G06F 1/1686* (2013.01)

(58) Field of Classification Search
CPC .. H10K 59/351; H10K 59/65; A61B 5/02108; A61B 5/02141; A61B 5/6898; G06F 3/011; G06F 1/1686
See application file for complete search history.

(56) References Cited

U.S. PATENT DOCUMENTS

| 9,049,998 B2 | 6/2015 | Brumback et al. |
| 2014/0092064 A1 | 4/2014 | Bernstein et al. |
| 2017/0086686 A1 | 3/2017 | Narasimhan et al. |

(Continued)

FOREIGN PATENT DOCUMENTS

| KR | 2019-0015688 A | 2/2019 |
| KR | 2021-0028302 A | 3/2021 |

(Continued)

*Primary Examiner* — Jennifer T Nguyen
(74) *Attorney, Agent, or Firm* — Innovation Counsel LLP

(57) ABSTRACT

Provided is a display device including a plurality of normal display pixel, one boost display pixel having a higher maximum luminance than the plurality of normal display pixels, and one light-receiving pixel disposed adjacent to the boost display pixel. Each of the normal display pixel, the boost display pixel, and the light-receiving pixel includes a first electrode, a second electrode, and an active layer, which is interposed between the first and second electrodes. The first electrodes of the normal display pixel, the boost display pixel, and the light-receiving pixel are disposed in the same layer. The second electrodes of the normal display pixel, the boost display pixel, and the light-receiving pixel are integrally connected to one another.

20 Claims, 28 Drawing Sheets

(56) References Cited

U.S. PATENT DOCUMENTS

| | | | | |
|---|---|---|---|---|
| 2019/0065717 A1* | 2/2019 | Won | .................... | G06V 40/1318 |
| 2021/0065625 A1 | 3/2021 | Wang et al. | | |
| 2021/0307697 A1* | 10/2021 | Hong | .................... | A61B 5/7278 |
| 2022/0115456 A1* | 4/2022 | Oh | ....................... | H10K 59/121 |
| 2022/0173174 A1* | 6/2022 | Hatsumi | ................ | H10K 59/65 |
| 2022/0293030 A1* | 9/2022 | Wu | ....................... | G09G 3/2003 |
| 2023/0055388 A1* | 2/2023 | Sakakibara | .......... | G09G 3/3275 |

FOREIGN PATENT DOCUMENTS

| | | |
|---|---|---|
| KR | 2021-0124609 A | 10/2021 |
| WO | 2020-165686 A1 | 8/2020 |

* cited by examiner

DISPLAY DEVICE

CROSS-REFERENCE TO RELATED APPLICATION

This application claims priority to Korean Patent Application No. 10-2021-0160608 filed on Nov. 19, 2021, and all the benefits accruing therefrom under 35 U.S.C. § 119, the content of which in its entirety is herein incorporated by reference.

BACKGROUND

1. Field

The present disclosure generally relates to a display device. More particularly, the present disclosure relates to a display device capable of measuring a blood pressure.

2. Description of the Related Art

Display devices, which are devices for displaying an image, are being used not only as TVs or monitors, but also as portable smartphones or tablet personal computers (PC). Particularly, a portable display device is a display device equipped with a variety of functions, such as the functions of a camera, a fingerprint sensor, and the like.

Meanwhile, with recent spotlight on the healthcare industry, various methods for acquiring biometric information with ease are being developed. For example, attempts are being made to replace traditional oscillometric blood pressure measurement devices with simple electronic products that are easy to carry around. However, most of electronic blood pressure measurement devices need their own light source, sensor, and display, and it is rather inconvenient to carry them around.

SUMMARY

Embodiments of the present disclosure provide a display device in which a light source and a light receiving unit are disposed adjacent to each other.

Embodiments of the present disclosure to provide a display device includes a plurality of normal display pixel, at least one boost display pixel having a higher maximum luminance than the plurality of normal display pixels, and at least one light-receiving pixel disposed adjacent to the at least one boost display pixel. Each of the plurality of normal display pixels, the at least one boost display pixel, and the at least one light-receiving pixel includes a first electrode, a second electrode, and an active layer, which is interposed between the first and second electrodes. The first electrode of each of the plurality of normal display pixels, the first electrode of the at least one boost display pixel, and the first electrode of the at least one light-receiving pixel are disposed in the same layer. The second electrode of each of the plurality of normal display pixels, the second electrode of the at least one boost display pixel, and the second electrode of the at least one light-receiving pixel are integrally connected to one another.

The maximum luminance of the at least one boost display pixel may be 1.5 times or greater than the maximum luminance of the plurality of normal display pixels.

The plurality of normal display pixels may include red normal display pixels, which emit red light, green normal display pixels, which emit green light, and blue normal display pixels, which emit blue light. The at least one boost display pixel may emit light of a green wavelength or longer.

The red normal display pixels, the green normal display pixels, and the blue normal display pixels may be alternately arranged in row and column directions. The at least one boost display pixel may emit red light or green light and may replace at least one normal display pixel that emits light of the same color as the at least one boost display pixel.

The at least one boost display pixel may emit red light or green light.

The at least one boost display pixel may have a larger emission area than the at least one normal display pixel emitting light of the same color as the at least one boost display pixel.

A light-emitting layer of the at least one boost display pixel may be thicker than a light-emitting layer of the at least one normal display pixel emitting light of the same color as the at least one boost display pixel.

A light-emitting layer of the at least one boost display pixel may include a first light-emitting material. The at least one normal display pixel emitting light of the same color as the at least one boost display pixel may include a second light-emitting material. The first light-emitting material may have a higher emission efficiency than the second light-emitting material.

The second light-emitting material may have a higher color reproducibility than the first light-emitting material.

The display device may further include a normal display pixel circuitry for driving the plurality of normal display pixels, and a boost display pixel circuitry for driving the at least one boost display pixel. The normal pixel circuitry may include more transistors than the boost display pixel circuitry.

Embodiments of the present disclosure to provide a display device includes a substrate including a display area, which includes a plurality of pixels, a plurality of first electrodes disposed in the pixels, on the substrate, a second electrode facing the first electrodes, and a plurality of active layers disposed in the pixels, between the first electrodes and the second electrode. Some of the pixels include normal display light-emitting layers as the active layers.

Some of the pixels include boost display light-emitting layers, which have a higher emission luminance than the normal display light-emitting layers, as the active layers. Some of the pixels include photoelectric conversion layers as the active layers.

A maximum luminance of the boost display light-emitting layers may be 1.5 times or greater than a maximum luminance of the normal display light-emitting layers.

The display area may include a boost display pixel area where the pixels including the boost display light-emitting layers are disposed and a light-receiving pixel area where the pixels including the photoelectric conversion layers are disposed. The boost display pixel area and the light-receiving pixel area may be disposed adjacent to each other.

The light-receiving pixel area may surround the boost display pixel area in a plan view.

The display area may include a boost display pixel/light-receiving pixel area where the pixels including the boost display light-emitting layers and the pixels including the photoelectric conversion layers may be alternately arranged to be adjacent to one another.

The display device may further include a pressure sensing member disposed on a bottom surface of the substrate or on a top surface of the second electrode.

Embodiments of the present disclosure to provide a display device includes a display unit including plurality of normal display pixels, at least one boost display pixel, which has a higher maximum luminance than the plurality of normal display pixels, and at least one light-receiving pixel, a sensor unit including a pressure sensor, and a control unit. The control unit includes an emission driving module, which controls the plurality of normal display pixels and the at least one boost display pixel to emit light or not to emit light and controls the amount by which the plurality of normal display pixels and the at least one boost display pixel are to emit light, a light reception data determination module, which receives an electrical signal from the at least one light-receiving pixel and determines light reception data based on the received electrical signal, a pulse wave signal generation module, which generates a pulse wave signal based on the light reception data, a pressure data determination module, which receives an electrical signal from the pressure sensor and determines pressure data based on the received electrical signal, and a blood pressure measurement module, which measures blood pressure based on the pulse wave signal and the pressure data.

In a blood pressure measurement mode, the emission driving module may control the at least one boost display pixel to emit light at a maximum luminance.

In a normal display mode, the emission driving module may control an amount of light to be emitted by the plurality of normal display pixels based on a gray level of the plurality of normal display pixels.

In the normal display mode, the emission driving module may control an amount of light to be emitted by the at least one boost display pixel, in accordance with gray data corresponding to a location of the at least one boost display pixel.

BRIEF DESCRIPTION OF THE DRAWINGS

The above and other features of the present disclosure will become more apparent by describing in detail embodiments thereof with reference to the accompanying drawings, in which.

DETAILED DESCRIPTION

Figure 1:
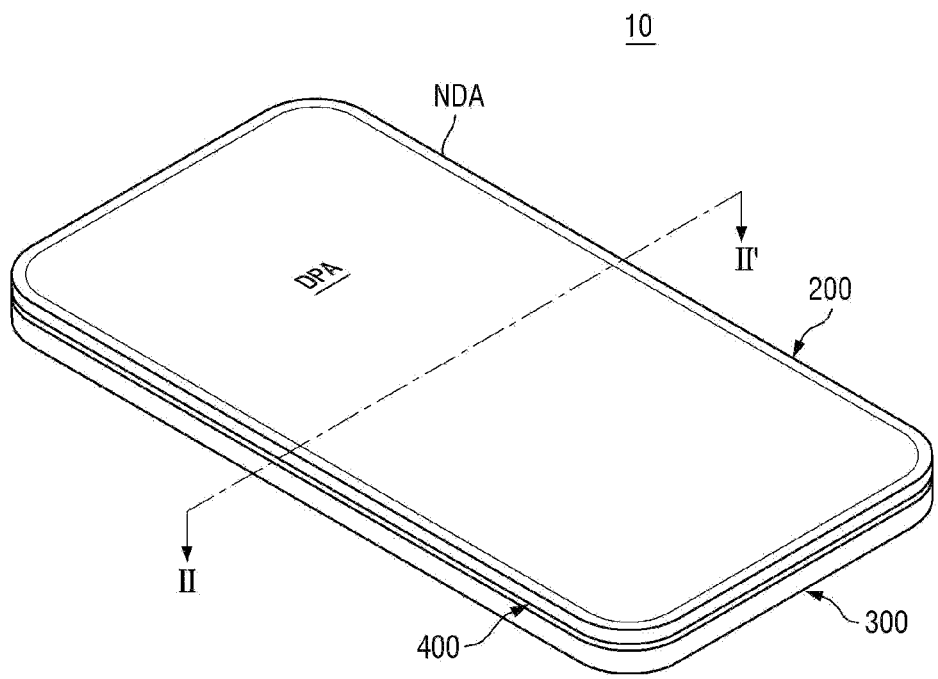
FIG. 1 is a perspective view of a display device according to an embodiment of the present disclosure.

The present disclosure now will be described more fully hereinafter with reference to the accompanying drawings, in which various embodiments are shown. This present disclosure may, however, be embodied in many different forms, and should not be construed as limited to the embodiments set forth herein. Rather, these embodiments are provided so that this disclosure will be thorough and complete, and will fully convey the scope of the present disclosure to those skilled in the art. Like reference numerals refer to like elements throughout.

It will also be understood that when a layer is referred to as being "on" another layer or substrate, it can be directly on the other layer or substrate, or intervening layers may also be present. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." "At least one of A and B" means "A and/or B." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the present disclosure present disclosure will be described in detail with reference to the accompanying drawings.

Figure 2:
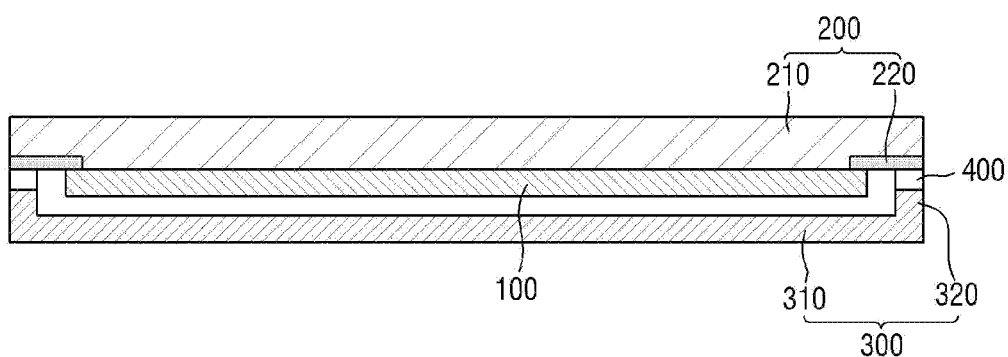
FIG. 2 is a cross-sectional view taken along line II-II' of FIG. 1.

FIG. 1 is a perspective view of a display device according to an embodiment of the present disclosure. FIG. 2 is a cross-sectional view taken along line II-II' of FIG. 1.

Referring to FIGS. 1 and 2, a display device 10 displays a moving image or a still image. Examples of the display device 10 include, but are not limited to, smartphones, mobile phones, tablet personal computers (PCs), personal digital assistants (PDAs), portable multimedia players (PMPs), televisions, game consoles, wristwatch-type electronic devices, head-mounted displays, PC monitors, notebook computers, car navigation systems, car dashboards, digital cameras, camcorders, electric billboards, various medical devices, various inspection devices, home appliances with display units (such as refrigerators and washing machines), and Internet-of-Things (IoT) devices.

The display device 10 may include a display area DPA and a non-display area NDA. The display area DPA may have a rectangular shape in a plan view, but the present disclosure is not limited thereto. Alternatively, the display area DPA may have various other shapes such as a square shape, a rhombus shape, a circular shape, or an elliptical shape in a plan view. The non-display area NDA may be disposed around the display area DPA. The non-display area NDA may surround the entire display area DPA or part of the display area DPA. Signal lines for applying signals to the display area DPA or transmitting signals detected from the display area DPA may be disposed in the non-display area NDA. The non-display area NDA may correspond to the bezel of the display device 10. FIGS. 1 and 2 illustrate that the non-display area NDA is disposed to surround the entire display area DPA, which has a rectangular shape, but the present disclosure is not limited thereto. Alternatively, the non-display area NDA may not be disposed on some of the sides of the display area DPA or may be bent toward the rear surface of the display area DPA to overlap with the display area DPA in a thickness direction, in which case, the non-display area NDA may not appear in a plan view.

The display device 10 may include a display panel 100, which provides light for forming an image. Examples of the display panel 100 may include a self-emission display panel such as an organic light-emitting diode (OLED) display panel, an inorganic electroluminescent (EL) display panel, a quantum-dot electrodynamics (QED) display panel, a micro-light-emitting diode (microLED) display panel, a nano-light-emitting diode (nanoLED) display panel, a plasma display panel (PDP), a field emission display (FED) panel, or a cathode-ray tube (CRT) display panel and a light-receiving display panel such as a liquid crystal display (LCD) panel or an electrophoretic display (EPD) panel. The display panel 100 will hereinafter be described as being, for example, an OLED display panel, which will hereinafter be referred to simply as the display panel 100, but the present disclosure is not limited thereto. That is, various other display panels may also be applicable to the display device 10.

The direction in which the display panel 100 provides light to the outside may be the thickness direction of the display panel 100. The display panel 100 may be classified into a front display panel, a rear display panel, or a both-sided display panel depending on the direction in which the display panel 100 provides light. Here, the term "front" may refer to a direction where elements (e.g., light-emitting elements) providing light are positioned with respect to a substrate 110 of the display panel 100 are positioned, and the term "rear" may refer to a direction opposite to the direction where the light-emitting elements are positioned.

In a case where the display panel 100 is a front display panel, the display panel 100 may provide light to one side in its thickness direction (e.g., in an upward direction), and a user may be able to see an image displayed by the display panel 100, from the top surface of the display panel 100. In a case where the display panel 100 is a rear display panel, the display panel 100 may provide light to the other side in its thickness direction (e.g., in a downward direction), and the user may be able to see an image displayed by the display panel 100, from the bottom surface of the display panel 100. In a case where the display panel 100 is a front display panel, light displaying an image does not penetrate an area where the substrate 110 is positioned. On the contrary, in a case where the display panel 100 is a rear display panel, light displaying an image can be seen through both the top and bottom surfaces of the display panel 100. The display panel 100 is illustrated as being a front display panel, but the present disclosure is not limited thereto.

The display device 10 may further include a window member 200, which is disposed above the display panel 100, and a cover member 300, which is disposed below the display panel 100. The window member 200 and the cover member 300 may have a larger size than the display panel 100 in a plan view.

The window member 200 may be disposed on the top surface of the display panel 100 from which light is emitted. The window member 200 may protect the display panel 100. The window member 200 may be formed of a transparent material and may thus transmit light emitted from the display panel 100 in the upward direction. The window member 200 may include, for example, tempered glass, ultra-thin tempered glass, or clear plastic as a window base 210, but the present disclosure is not limited thereto.

The window member 200 may further include a printed layer 220, which is disposed on the window base 210. The printed layer 220 may have a chromatic color or an achromatic color such as black, gray, or white. The printed layer 220 may block light and may be disposed mostly in the non-display area NDA. All or at least some of the edges of the non-display area NDA may be defined by the printed layer 220 in a plan view.

The cover member 300 may protect the display panel 100 from below the display panel 100. The cover member 300 may include a bottom part 310 and sidewall parts 320, which are disposed along the edges of the bottom part 310. The space defined by the bottom part 310 and the sidewall parts 320 may be used as space for accommodating the display panel 100 therein. A battery or a printed circuit board (PCB) including integrated circuits (ICs) may be disposed between the display panel 100 and the cover member 300.

The window member 200 and the cover member 300 may form the exterior of the display device 10 together. As the location of the cover member in the display device 10 is irrelevant to the direction where light for forming an image is emitted, the cover member 300, unlike the window member 200, may be formed of an opaque material. The cover member 300 may be formed of a metallic material or a plastic material, but the present disclosure is not limited thereto.

The sidewall parts 320 of the cover member 300 may be attached and bonded to the bottom surface or the sides of the window member 200 via a bonding layer 400. In this case, the display panel 100 may be completely received in the space between the window member 200 and the cover member 300 that are completely bonded together, and the exterior of the display device 10 may be defined by the cover member 300, the window member 200, and/or the bonding layer 400. The bonding layer 400 may include an adhesive tape, an adhesive resin, or a curable resin. Alternatively, the bonding layer 400 may include a waterproof tape and/or a waterproof resin and may thus provide a waterproof function to the display device 10.

Although not specifically illustrated, a mold frame may be further disposed between the cover member 300 and the window member 200.

Figure 3:
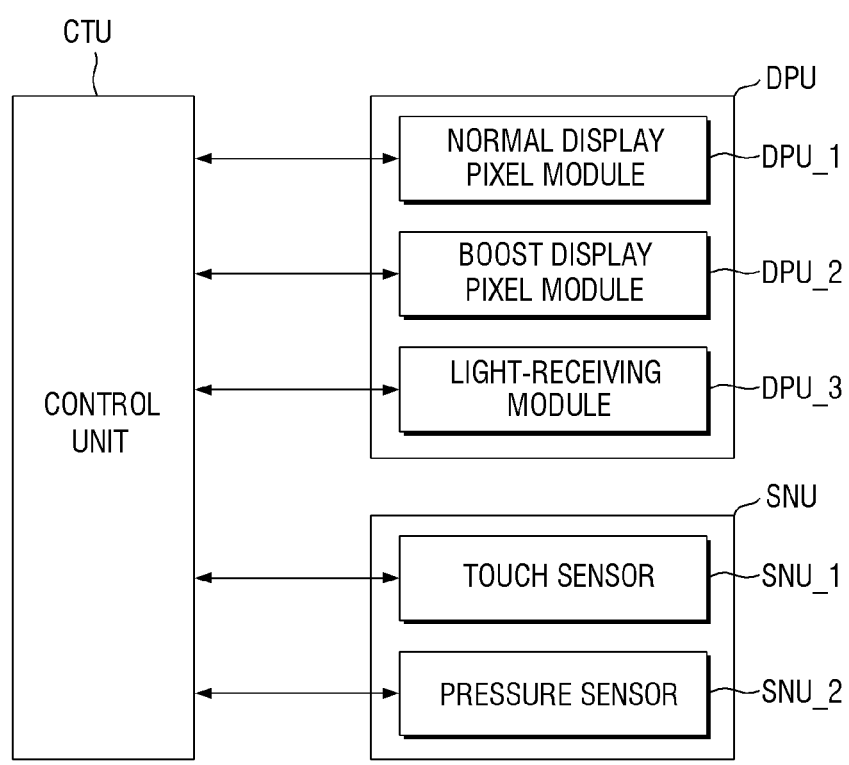
FIG. 3 is a block diagram of the display device of FIG. 1.

FIG. 3 is a block diagram of the display device of FIG. 1.

Referring to FIG. 3, the display device 10 may include a display unit DPU, a sensing unit SNU, and a control unit CTU.

The display unit DPU may include display pixel modules (DPU_1 and DPU_2) and a light-receiving module DPU_3.

The display pixel modules (DPU_1 and DPU_2) may include normal display pixel module DPU_1, which includes a plurality of normal display pixels, and a boost display pixel module DPU_2, which includes one or more boost display pixels. The boost display pixels have a higher maximum luminance than the normal display pixels. The boost display pixels, which have a relatively high maximum luminance, not only display an image together with the normal display pixels, but also increase the amount of light incident on the light-receiving module DPU_3 to improve the precision of sensing via the light-receiving module DPU_3. Here, the term "maximum luminance" does not mean a theoretical maximum luminance based on light-emitting diodes (LEDs), but means an actual maximum luminance that can be reached under normal driving conditions.

The light-receiving module DPU_3 may include at least one unit light-receiving module. Although not shown, the unit light-receiving module may be positioned between the normal display pixels and the boost display pixels in a plan view. The unit light-receiving module may receive light incident in a direction opposite to the direction where light is output from the display pixel modules (DPU_1 and DPU_2) and may generate electric data having the amount of the incident light reflected therein.

The display pixel modules (DPU_1 and DPU_2) and the light-receiving module DPU_3 of the display unit DPU may all be incorporated into, and disposed in, the display panel 100.

In a case where the display pixel modules (DPU_1 and DPU_2) of the display unit DPU include not only the normal display pixels, but also the boost display pixels, an additional light source for measuring blood pressure may not be provided. In addition, in a case where the boost display pixels of the display unit DPU are incorporated into the display panel 100 together with the light-receiving module DPU_3, the amount of light received can be increased by reducing the path of light incident upon the light-receiving module DPU_3. In addition, a circuit layer in which thin film transistors of each pixel are disposed and a layer in which the light-emitting element of each pixel is disposed can be shared by arranging the normal display pixels and the boost display pixels of the display pixel modules (DPU_1 and DPU_2) and light-receiving pixels of the light-receiving module DPU_3 in the circuit layer, and as a result, the efficiency of the manufacture of the display device 10 can be improved. The normal display pixels of the normal display pixel module DPU_1 and the boost display pixels of the boost display pixel module DPU_2 and the light-receiving pixels of the light-receiving module DPU_3 will be described later in detail.

The sensing unit SNU may include a touch sensor SNU_1 and a pressure sensor SNU_2. The touch sensor SNU_1 may sense touch input from the user, and the pressure sensor SNU_2 may sense the magnitude of pressure applied to the display device 10.

Each of the touch sensor SNU_1 and the pressure sensor SNU_2 may be provided as one or more layers and may be integrally formed with the display panel 100. Alternatively, each of the touch sensor SNU_1 and the pressure sensor SNU_2 may be provided as a separate film or panel and may then be attached to the display panel 100. The touch sensor SNU_1 and the pressure sensor SNU_2 may be incorporated into a single member, or a single sensing layer may be provided to perform the functions of each of the touch sensor SNU_1 and the pressure sensor SNU_2 may.

The control unit CTU may drive and control the display unit DPU and the sensing unit SNU. Also, the control unit CTU may receive and interpret information sensed from the display unit DPU and/or from the sensing unit SNU and may provide the result of the interpretation to the display unit DPU as data so that the data may be displayed via the display unit DPU.

The control unit CTU may include one or more ICs. For example, the control unit CTU may be provided as at least one IC chip. The control unit CTU may be electrically connected to the display panel 100 and/or sensors via lines or via a communication network. At least part of the control unit CTU may be provided as a driving chip and may be directly attached on the display panel 100.

The cross-sectional structures of display devices according to embodiments of the present disclosure will hereinafter be described.

Figure 4:
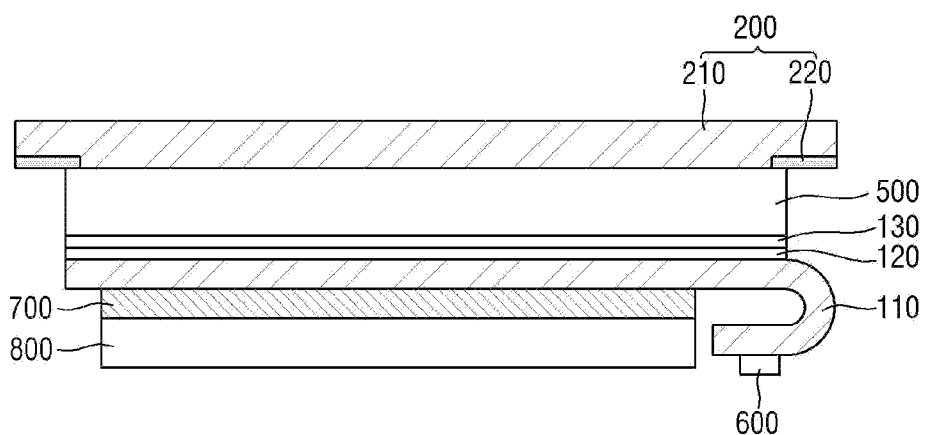
FIG. 4 is a cross-sectional view of the display device of FIG. 1.

FIG. 4 is a cross-sectional view of the display device of FIG. 1.

Referring to FIGS. 3 and 4, the display device 10 may include the window member 200, which is disposed on one surface of the display panel 100, a transparent bonding layer 500, which is disposed between the display panel 100 and the window member 200, a pressure sensing member 700, which is attached to the bottom surface of the display panel 100, and a driving IC 600, which is mounted on the surface of the display panel 100.

The display unit DPU and the touch sensor SNU_1 may be positioned in the display panel 100. Specifically, the display panel 100 may include a substrate 110, a display layer 120, which is disposed on the substrate 110, and a touch layer 130, which is disposed on the display layer 120. The display unit DPU may be provided in the display layer 120, and the touch sensor SNU_1 may be provided in the touch layer 130.

The substrate 110 may have flexibility. The substrate 110 may be bendable, foldable, and stretchable. The substrate 110 may be bent to have one end part face the bottom of the substrate 110. A driving unit such as the driving IC 600 may be disposed on an end part of the bent substrate 110. The driving IC 600 may be mounted on one surface of the bent substrate 110. The driving IC 600 may be attached directly to the surface of the substrate 110 via an anisotropic conductive film or via ultrasonic bonding. The size of the non-display area NDA can be reduced by bending an area where the driving unit is disposed in the downward direction.

The display layer 120 is disposed on the substrate 110. The display layer 120 may include a circuit layer and a light-emitting layer and a light-receiving layer, which are disposed on the circuit layer. The circuit layer receives driving signals from the control unit CTU and controls the amount and duration of emission of the light-receiving layer. In addition, the circuit layer transmits electrical charge generated by the light-receiving layer. Part of the control unit CTU may be mounted on one surface of the substrate 110 as the driving IC 600, but the present disclosure is not limited thereto.

The touch layer 130 is disposed on the display layer 120. The touch layer 130 recognizes touch input from, for example, a user. As the touch layer 130 is positioned on the path of emission of the display layer 120, the touch layer 130 may have a predetermined level of transparency to avoid hiding the display screen of the display panel 100 or not to lower luminance the luminance of the display panel 100.

The touch layer 130 may include one or more touch electrodes and may further include one or more insulating films. The touch electrodes may include a conductive material. The conductive material may include an opaque, low-resistance metal such as aluminum (Al), titanium (Ti), or magnesium (MG), a transparent conductive oxide such as indium tin oxide (ITO), indium zinc oxide (IZO), zinc oxide (ZnO), or indium tin zinc oxide (ITZO), or a transparent conductive material such as a conductive polymer (e.g., poly(3,4-ethylenedioxythiophene) (PEDOT)), metallic nanowires, or graphene. In a case where the touch electrodes include an opaque material, the touch electrodes may be arranged in a mesh shape and may thus secure transparency as a whole. In a case where the touch electrodes include a transparent material, the touch electrodes may be formed in a planar shape such as a rhombus shape. However, the material and the shape of the touch electrodes are not particularly limited.

A transparent insulating material may be used as the material of the insulating films of the touch layer 130.

The touch electrodes may be formed directly on the display layer 120. Here, the touch electrodes may be disposed directly on the display layer 120 without any adhesive layer interposed therebetween or with another layer such as an insulating film present therebetween.

The transparent bonding layer 500 is disposed on the touch layer 130, and the window member 200 is disposed on the transparent bonding layer 500. The window member 200 may be coupled to the display panel 100 via the transparent bonding layer 500. An optically clear material such as an optically clear adhesive (OCA) or an optically clear resin (OCR) may be used as the material of the transparent bonding layer 500, but the present disclosure is not limited thereto. Alternatively, a pressure sensitive adhesive (PSA), an adhesive, or another resin that can secure a predetermined level of transparency may also be used as the material of the transparent bonding layer 500.

The pressure sensing member 700 may include the pressure sensor SNU_2. The pressure sensor SNU_2 may include one or more pressure sensing electrodes and may further include an insulating film. The pressure sensor SNU_2 may be provided in the form of, a force sensor, a strain gauge, or a gap capacitor, but the present disclosure is not limited thereto.

The pressure sensing member 700 may be disposed on the bottom surface of the display panel 100. That is, the pressure sensing member 700 may be disposed on the bottom surface of the substrate 110. The pressure sensing member 700 may sense the pressure applied to the display device 10. When the user is touching on the uppermost surface of the display device 10 (e.g., the top surface of the window member 200), the touch coordinates of the touch input from the user may be sensed by the touch layer 130, and the pressure of the touch input may be sensed by the pressure sensing member 700. The pressure sensed by the pressure sensing member 700 may be used as a type of user input together with the touch input. Also, the pressure sensing member 700 may be used to measure the blood pressure of the user, together with the light-receiving module DPU_3 of the display unit DPU. A method of measuring the blood pressure of the user using the pressure sensing member 700 and the light-receiving module DPU_3 will be described later.

The pressure sensing member 700 may be provided as a panel or a film and may be attached to the bottom surface of the display panel 100 via a bonding layer such as a PSA. As the pressure sensing member 700 is not positioned on the emission path of light from the display layer 120, the pressure sensing member 700 does not need to be transparent.

The display device 10 may further include a buffer member 800. The buffer member 800 may have elasticity and may absorb external shock. As external shock can be absorbed by the buffer member 800, damage to the display device 10 can be prevented. The buffer member 800 may be attached to the bottom surface of the pressure sensing member 700. The buffer member 800 may be formed of polyurethane, but the present disclosure is not limited thereto. The buffer member 800 may be provided as a film.

Alternatively, the locations of the buffer member 800 and the pressure sensing member 700 relative to each other may change. Specifically, the buffer member 800 may be attached to the bottom surface of the display panel 100, and the pressure sensing member 700 may be attached to the bottom surface of the buffer member 800. In this case, as a pressuring event from the user through the top surface of the window member 200 is absorbed by the buffer member 800, pressure may not be able to be precisely detected. Also, in a case where the substrate 110 of the display panel 100 has flexibility, the support member (see "810" of FIG. 5) for maintaining the shape of the substrate 110 and reinforcing the strength of the substrate 110 is needed, and the buffer member 800 alone is not enough to perform such functions. In this case, however, the total thickness of the display device 10 may increase, and it may be difficult to precisely detect pressure.

On the contrary, as illustrated in FIG. 4, in a case where the pressure sensing member 700 is interposed between the display panel 100 and the buffer member 800, pressure can be precisely detected because of the absence of the buffer member 800 on the path of transmission of pressure from the top surface of the window member. The pressure sensing member 700 may have a lower elasticity than the buffer member 800 and may have a greater rigidity and mechanical strength than the buffer member 800. In a case where the pressure sensing member 700 has a thickness of about 30 μm, the pressure sensing member 700 may help maintain the shape of the substrate 110, which is flexible, without a requirement of an additional support member. Accordingly, cost that may be incurred by the provision of an additional support member can be reduced, the thickness of the display device 10 can be reduced, and the precision of detection of pressure can be enhanced.

Figure 5:
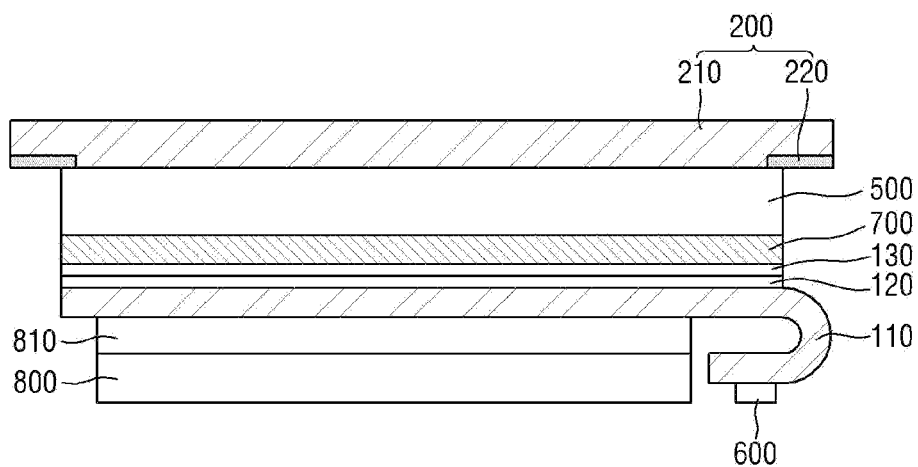
FIG. 5 is a cross-sectional view of a display device according to another embodiment of the present disclosure.

FIG. 5 is a cross-sectional view of a display device according to another embodiment of the present disclosure.

Referring to FIG. 5, a display device 11 differs from the display device 10 of FIG. 4 in that a pressure sensing member 700 is disposed on the top surface of a display panel 100 and a support member 810 is disposed between the bottom surface of the display panel 100 and a buffer member 800.

Specifically, the pressure sensing member 700 is disposed between the display panel 100 and a window member 200. The pressure sensing member 700 is disposed on a touch layer 130 of the display panel 100. A transparent bonding layer 500 and the window member 200 are disposed on the pressure sensing member 700.

The pressure sensing member 700 may be provided as a panel or a film or as a pressure sensing layer. In a case where the pressure sensing member 700 is provided as a panel or a film, the pressure sensing member 700 may be attached on the display panel 100 via a transparent bonding layer (not illustrated) such as an OCA.

In a case where the pressure sensing member 700 is provided as a pressure sensing layer, pressure sensing electrodes of the pressure sensing layer may be formed directly on the touch layer 130. In this case, the pressure sensing member 700 may be embedded in the display panel 100 together with a display layer 120 and the touch layer 130.

The pressure sensing member 700 may be positioned on the path of emission of light from the display layer 120. Thus, the pressure sensing member 700 may have a predetermined level of transparency to avoid hiding the display screen of the display panel 100 or not to lower the luminance of the display panel 100. To accomplish this, the pressure sensing electrodes of the pressure sensing member 700 may include a transparent conductive material that may be included in touch electrodes or may include a low-resistance metal arranged in a mesh shape. However, the material of the pressure sensing electrodes is not particularly limited.

In the embodiment of FIG. 5, like in the embodiment of FIG. 4, the buffer member 800 may be disposed on the bottom surface of the display panel 100, and the support member 810 may be further disposed between the bottom surface of the display panel 100 and the buffer member 800. The support member 810 may support the rigidity of a substrate 110, which has flexibility. The support member 810 may include a polymer film such as a polyethylene terephthalate (PET) film, a polycarbonate (PC) film, or a polymethyl methacrylate (PMMA) film. The support member 810 may further include a heat dissipation layer, an electromagnetic wave shielding layer and/or a light-blocking layer.

As the pressure sensing member 700 is positioned on the display panel 100, the path of transmission of pressure can be shortened via the window member 200. Thus, the pressure sensing sensitivity of the pressure sensing member 700 can be improved.

Alternatively, the pressure sensing member 700 may be disposed between the display layer 120 and the touch layer 130 (or a film- or panel-type touch sensor).

Figure 6:
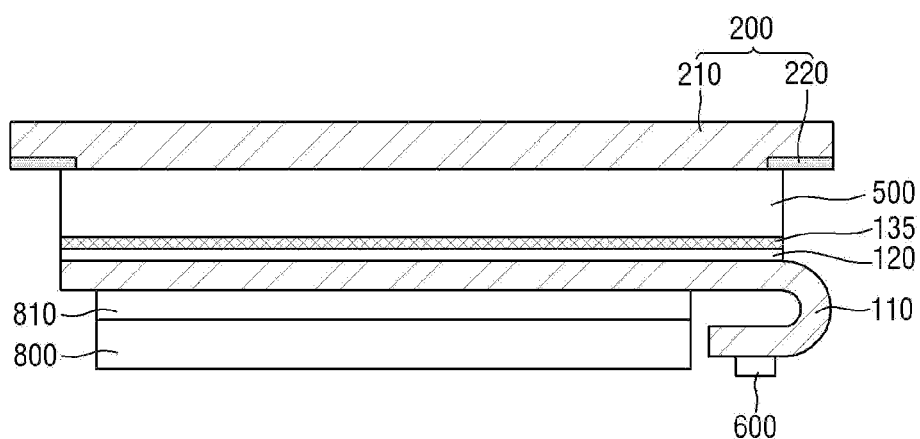
FIG. 6 is a cross-sectional view of a display device according to another embodiment of the present disclosure.

FIG. 6 is a cross-sectional view of a display device according to another embodiment of the present disclosure.

Referring to FIG. 6, a display device 12 differs from the display device 11 in that a touch/pressure sensing layer 135 where a touch layer and a pressure sensing layer are incorporated is provided. That is, the pressure sensing member 700 may not be disposed between the transparent bonding layer 500 and the display panel 100. The touch/pressure sensing layer 135 may include not only touch electrodes, but also pressure sensing electrodes. In the touch/pressure sensing layer 135, the touch electrodes may not overlap the pressure sensing electrodes in a thickness direction. For example, one or more touch electrodes may perform the functions of pressure sensing electrodes. In another example, the touch electrodes and the pressure sensing electrodes are separate from one another in a plan view, but may share one or more conductive layers that form electrodes and wires. For example, the pressure sensing electrodes may be formed of a conductive layer positioned on the same layer as a conductive layer forming the touch electrodes or the wires of the touch electrodes. Similarly, the wires of the pressure sensing electrodes may also be formed of a conductive layer positioned on the same layer as the conductive layer forming the touch electrodes or the wires of the touch electrodes.

As a touch layer and a pressure sensing layer are incorporated into the touch/pressure sensing layer 135, the thickness of the display device 12 can be reduced.

Figure 7:
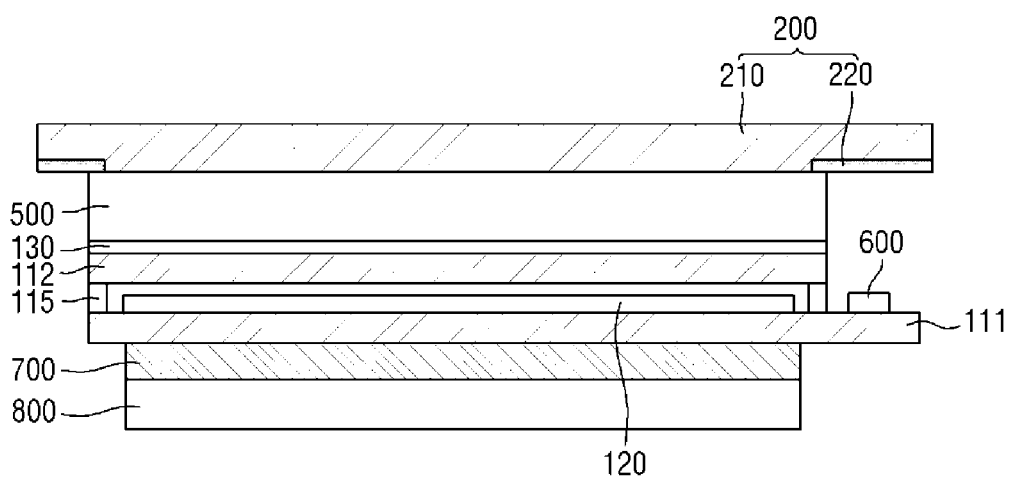
FIG. 7 is a cross-sectional view of a display device according to another embodiment of the present disclosure.

FIG. 7 is a cross-sectional view of a display device according to another embodiment of the present disclosure.

Referring to FIG. 7, a display panel of a display device 13 may include a first substrate 111, which is rigid.

The display panel includes the first substrate 111, which is formed of a rigid material such as glass, and a display layer 120 is disposed on the first substrate 111. A second substrate 112, which is formed of a rigid material such as glass, is disposed on the display layer 120. The second substrate 112 may face the first substrate 111 and may be bonded to the first substrate 111 along the edges thereof via a sealing member 115. One end portion of the first substrate 111 may protrude outward from one end portion of the second substrate 112, and a driving IC 600 may be mounted on one surface of the end portion of the first substrate 111.

A touch layer 130 is provided on one surface of the second substrate 112, and a transparent bonding layer 500 and a window member 200 are sequentially stacked on the touch layer 130.

A pressure sensing member 700 may be attached to the bottom surface of the first substrate 111, and a buffer member 800 may be disposed on the bottom surface of the pressure sensing member 700.

Although not specifically illustrated, the pressure sensing member 700 may be disposed on the display panel, as illustrated in FIG. 5, or may be incorporated together with the touch layer 130, as illustrated in FIG. 6.

The display devices 10, 11, 12, and 13 not only can display an image, but also can be useful for detecting touch input and measuring pressure. Also, as the display layer 120 of the display panel 100 includes the display pixel modules (DPU_1 and DPU_2) and the light-receiving module DPU_3, the display layer 120 of the display panel 100 can be used to recognize a fingerprint of the user. For example, in response to the user touching the window member 200 with a finger, light emitted from the display pixel modules (DPU_1 and DPU_2) may be reflected from the finger of the user and may then be received by the light-receiving module DPU_3. As the ridges and valleys of a fingerprint have different reflectivities, the shape of the fingerprint can be estimated based on the amount of light incident upon each of the unit light-receiving module of the light-receiving module DPU_3.

In addition, the display devices 10, 11, 12, and 13 can be used to measure the blood pressure of a user. It will hereinafter be described how to measure blood pressure with the use of a display device.

Figure 8:
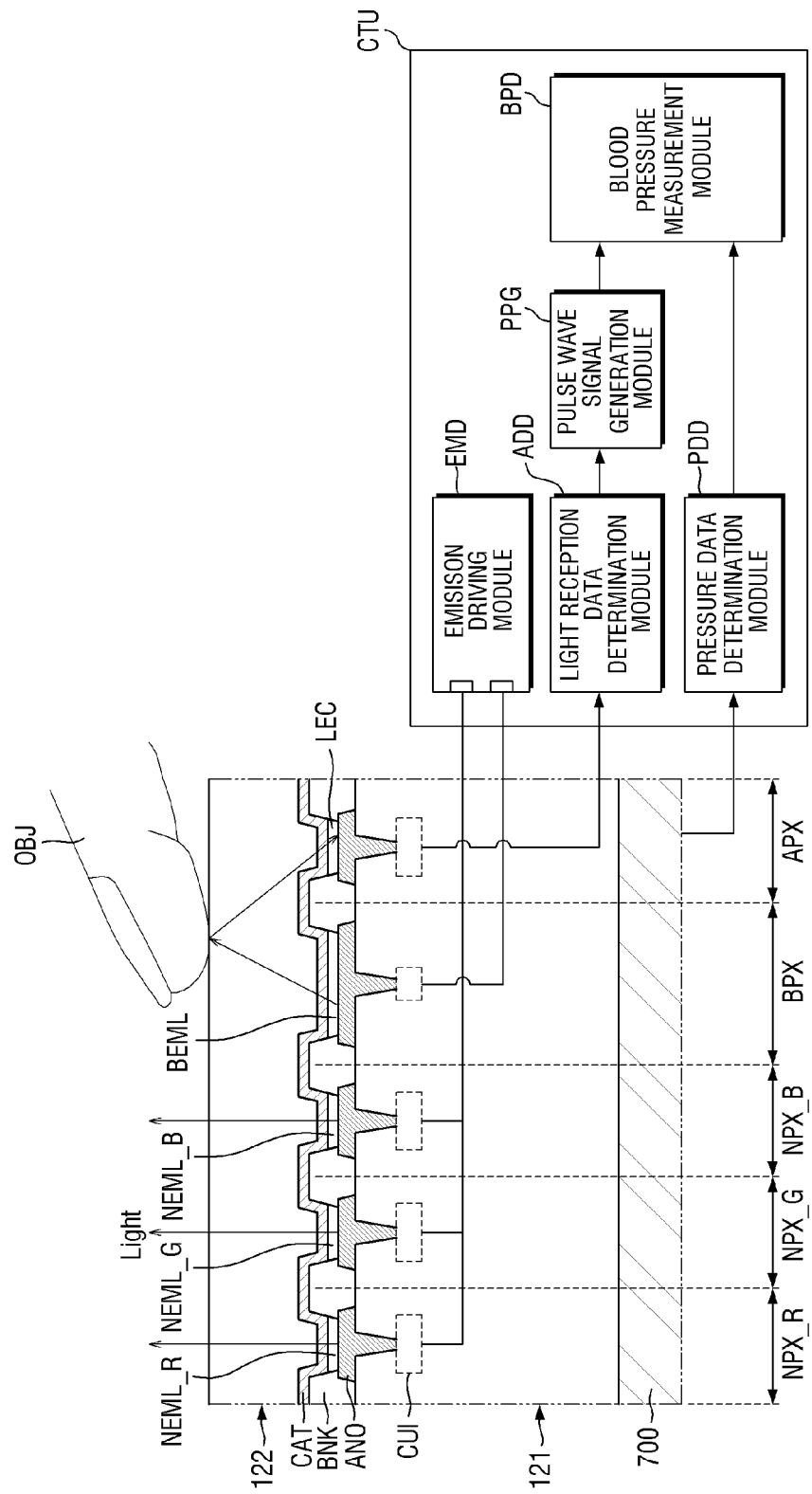
FIG. 8 illustrates a method of measuring blood pressure through light-emitting and light-receiving operations of a display device according to an embodiment of the present disclosure.
Figure 9A:
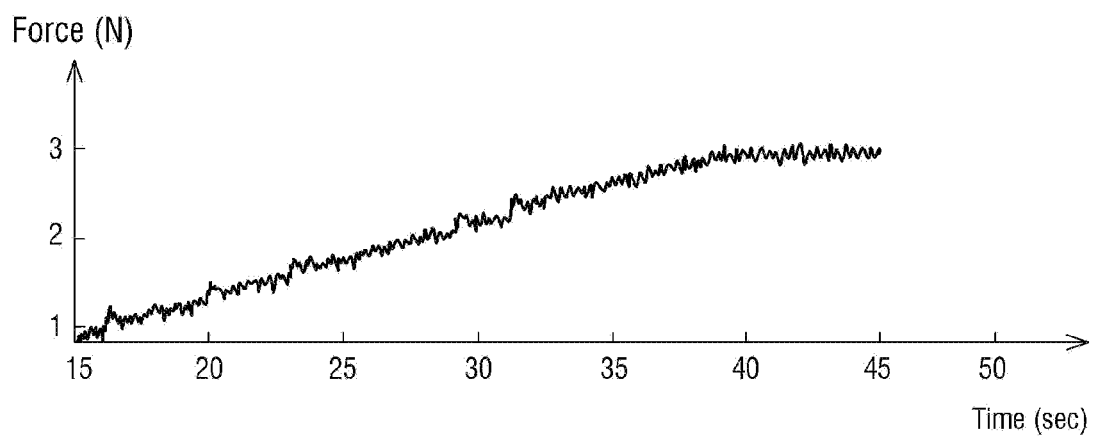
FIG. 9A is a graph showing the variation of a pulse wave signal over pressing time.
Figure 9B:
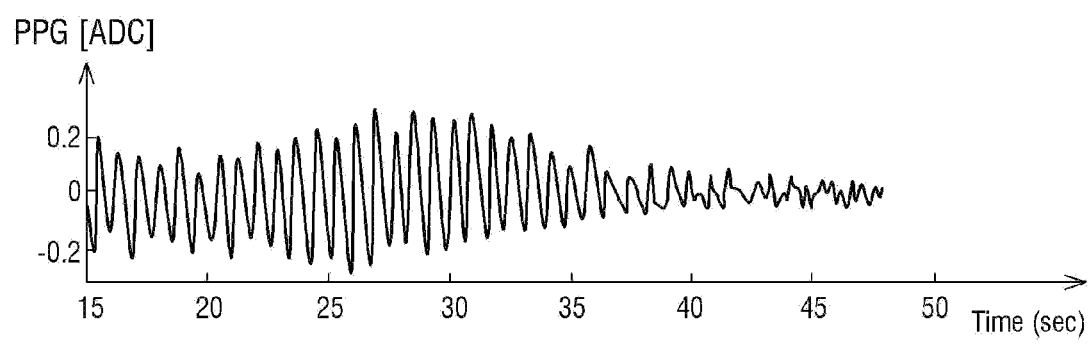
FIG. 9B is a graph showing the variation of pressure over pressing time.
Figure 9C:
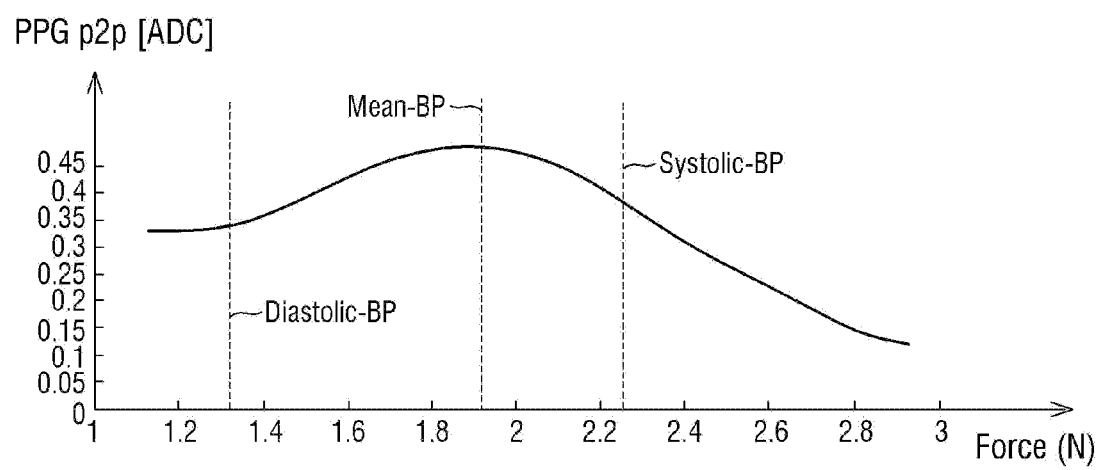
FIG. 9C is a graph showing the variation of a pulse wave signal against pressure.

FIG. 8 illustrates a method of measuring blood pressure through light-emitting and light-receiving operations of a display device according to an embodiment of the present disclosure. FIG. 9A is a graph showing the variation of a pulse wave signal over pressing time. FIG. 9B is a graph showing the variation of pressure over pressing time. FIG. 9C is a graph showing the variation of a pulse wave signal against pressure.

FIG. 8 illustrates three normal display pixels NPX and one boost display pixel BPX. A unit light-receiving module may have a similar configuration and a stack structure to display pixels (NPX and BPX) of each of the display pixel modules (DPU_1 and DPU_2). The unit light-receiving module may also be referred to as a light-receiving pixel APX.

The three normal display pixels NPX, i.e., first, second, and third normal display pixels NPX_R, NPX_G, and NPX_B, emit light of different colors. For example, the first, second, and third normal display pixels NPX_R, NPX_G, and NPX_B may emit red light, green light, and blue light, respectively. A plurality of first normal display pixels NPX_R, a plurality of second normal display pixels NPX_G, and a plurality of third normal display pixels NPX_B may be provided and may be alternately arranged in rows and columns in a plan view. Various colors can be implemented by combining multiple beams of light emitted from neighboring normal display pixels NPX (see "DOT" of FIG. 11).

The boost display pixel BPX emits light of a particular wavelength. The wavelength of the light emitted by the boost display pixel BPX may be longer than the wavelength of blue light and may be the same as, or longer than, the wavelength of green light. For example, the boost display pixel BPS may emit green light, red light, or infrared light. In a case where the boost display pixel BPX emits light of the same color as the normal display pixels NPX, the wavelength of the light emitted by the boost display pixel BPX may be the same as, or different from, the wavelength of the light emitted by the normal display pixels NPX.

In a case where a plurality of boost display pixels BPX are provided, all the plurality of boost display pixels BPX may emit light of the same color. Alternatively, the plurality of boost display pixels BPX may include boost display pixels BPX displaying two or more different colors such as a boost display pixel BPX displaying red light and a boost display pixel BPX displaying green light.

The maximum luminance of light emitted by the boost display pixel BPX may be higher than the maximum luminance of the normal display pixels NPX. The light emitted by the boost display pixel BPX may be used in sensing light via the light-receiving pixel APX. Also, the light emitted by the boost display pixel BPX may be used to display an image together with the normal display pixels NPX, but the present disclosure is not limited thereto. Alternatively, the light emitted by the boost display pixel BPX may be used exclusively for sensing.

The light-receiving pixel APX may be disposed adjacent to the boost display pixel BPX and may have a similar stack structure to the display pixels (NPX and BPX). The light-receiving pixel APX may be disposed adjacent to the boost display pixel BPX. The light-receiving pixel APX may convert the amount of light received into an electrical signal.

The light received by the light-receiving pixel APX may include light originated from the boost display pixel BPX, light originated from the normal display pixels NPX, and/or external light incident from the outside regardless of the display pixels (NPX and BPX). As a finger OBJ of a user is located near the top surface of the window member 200 during a blood pressure measurement process or a fingerprint sensing process, the influence of the external light limited, and most of the light received by the light-receiving pixel APX may originate from the display pixels (NPX and BPX). As the boost display pixel BPX is disposed adjacent to the light-receiving pixel APX and has a higher luminance than the normal display pixels NPX, light emitted from the boost display pixel BPX and then reflected from the finger OBJ may play a dominant role in determining the amount of light received by the light-receiving pixel APX.

Each of the display pixels (NPX and BPX) and the light-receiving pixel APX include a first electrode ANO, a second electrode CAT, and an active layer (NEML, BEML, or LEC), which is interposed between the first electrode ANO and the second electrode CAT. The first electrode ANO, the active layer (NEML, BEML, or LEC), and the second electrode CAT may form a diode.

The first electrodes ANO of the display pixels (NPX and BPX) and the light-receiving pixel APX are separate from one another. The second electrodes CAT of the display pixels (NPX and BPX) and the light-receiving pixel APX may be a common electrode connected in common to the display pixels (NPX and BPX) and the light-receiving pixel APX. An active layer NEML_R of the first normal display pixel NPX_R may be a red light-emitting layer, an active layer NEML_G of the second normal display pixel NPX_G may be a green light-emitting layer, and an active layer NEML_B of the third normal display pixel NPX_B may be a blue light-emitting layer. An active layer BEML of the boost display pixel BPX may be a red light-emitting layer. An active layer LEC of the light-receiving pixel APX may be a photoelectric conversion layer.

The first electrodes ANO of pixels (NPX, BPX, and APX) are disposed on a circuit layer 121. A bank layer BNK may be provided between the pixels (NPX, BPX, and APX) to divide the pixels (NPX, BPX, and APX).

Pixel circuits CUT, which drive the pixels (NPX, BPX, and APX), are disposed on the circuit layer 121. The pixel circuits CUI may be connected to the first electrodes ANO of the pixels (NPX, BPX, and APX). The pixel circuits CUI may include transistors.

Pixel circuits CUI connected to the first electrodes ANO of the first, second, and third normal display pixels NPX_R, NPX_G, and NPX_B may all have the same structure. A pixel circuit CUI connected to the first electrode ANO of the boost display pixel BPX may have the same structure as, or a different structure from, the pixel circuits CUI connected to the first electrodes ANO of the first, second, and third normal display pixels NPX_R, NPX_G, and NPX_B and may include fewer transistors than the pixel circuits CUI connected to the first electrodes ANO of the first, second, and third normal display pixels NPX_R, NPX_G, and NPX_B. A pixel circuit CUI connected to the first electrode ANO of the light-receiving pixel APX may have a different structure from the pixel circuits CUI connected to the first electrodes ANO of the normal display pixels NPX and the first electrode ANO of the boost display pixel BPX. The number of transistors included in the pixel circuit CUI connected to the first electrode ANO of the light-receiving pixel APX may be smaller than the number of transistors included in each of the pixel circuits CUI connected to the first electrodes ANO of the normal display pixels NPX, but the present disclosure is not limited thereto.

Although the pixel circuits CUI may have different structures for the normal display pixels NPX, the boost display pixel BPX, and the light-receiving pixel APX, the transistors of each of the pixel circuits CUI may share the same material layers. Thus, the transistors of each of the pixel circuits CUI may have substantially the same stack structure regardless of their functions, but the present disclosure is not limited thereto. The pixel circuits CUI of the circuit layer 121 may include both P-type metal-oxide semiconductor (PMOS) transistors, which use polysilicon as a semiconductor layer, and N-type metal-oxide semiconductor (NMOS) transistors, which use an oxide semiconductor as a semiconductor layer.

A control unit CTU may include an emission driving module EMD, a pressure data determination module PDD, a light reception data determination module ADD, a pulse wave signal generation module PPG, and a blood pressure measurement module BPD.

The emission driving module EMD may control whether and the amount by which the normal display pixels NPX and/or the boost display pixel BPX emit light via the pixel circuits CUI. In a normal display mode, the emission driving module EMD may control the amount of light to be emitted by the normal display pixels NPX based on the gray level of the normal display pixels NPX. The emission driving module EMD may control the boost display pixel BPX not to emit light in the normal display mode or may control the amount of emission of the boost display pixel BPX based on gray data for the location of the boost display pixel BPX. In a blood pressure measurement mode, the emission driving module EMD controls the boost display pixel BPX to emit light at its maximum luminance. In the blood pressure measurement mode, the amount of emission of the normal display pixels NPX may be controlled based on the gray level of the normal display pixels NPX, or the normal display pixels NPX may be controlled to emit light at its maximum luminance.

The pressure data determination module PDD determines pressure data for the magnitude of pressure applied based on an electrical signal received from the pressure sensing member 700.

The light reception data determination module ADD determines light reception data for the amount of light collected by the light-receiving pixel APX based on an electrical signal received from the light-receiving pixel APX.

The pulse wave signal generation module PPG receives the light reception data and generates a photoplethysmography (PPG) signal based on the light reception data. The PPG signal, which is a waveform indicating changes in blood vessel volume in a peripheral region during pulsation, may be generated based on the light reception data.

Specifically, referring to FIGS. 8 and 9A, during the systole of a human heart, the blood pumped from the left ventricle of the human heart moves to the peripheral tissues, and the blood volume on the arterial side increases. In addition, during the systolic phase of the heart, red blood cells carry more oxygenated hemoglobin to the peripheral tissues. During the diastolic phase of the human heart, there exists a partial suction of blood from the peripheral tissues toward the human heart. Thus, if light from the display pixels (NPX, BPX, and APX) is irradiated onto the peripheral blood vessels, the light may be absorbed by the peripheral tissues. As light absorption depends on hematocrit and blood volume. Light absorption may be maximized during the systolic phase of the heart and may be minimized during the diastolic phase of the heart. As light absorption is inversely proportional to the amount of incident light, light absorption may be estimated based on light reception data corresponding to the amount of light incident upon the light-receiving pixel APX, and an PPG signal of FIG. 9A may be generated based on the estimated light absorption.

The PPG signal reflects the maximum light absorption during the systolic phase of thehuman heart and reflects the minimum light absorption during the diastolic phase of the human heart. In addition, the PPG signal fluctuates in accordance with the cycle of heartbeats. As the PPG signal reflects blood pressure changes between heartbeats, blood pressure can be measured using the PPG signal.

To measure blood pressure, which is synchronized with heartbeats, not only the PPG signal, but also pressure data is needed. Referring to FIGS. 8 and 9B, as the user places a finger in contact with the display device 10 and detaches the finger from the display device 10, the pressure (or contact pressure) applied to the pressure sensing member 700 gradually increases, reaches its maximum, and then gradually decreases. When the contact pressure increases, the blood vessels constrict, resulting in a small or zero blood flow. When the contact pressure decreases, the blood vessels dilate and blood begins to flow again. A further decrease in the contact pressure results in a greater blood flow. As a change in the amount of light absorbed by the light-receiving pixel APX is proportional to a change in blood flow and the light-receiving pixel APX receives as much light as the amount of light absorbed by the finger subtracted from the total amount of incident light, a change in the amount of light received by the light-receiving pixel APX reflects a change in blood flow. Accordingly, a change in blood flow, which is synchronized with heartbeats, can be detected based on light-received data from the light-receiving pixel APX. The blood pressure measurement module BPD may estimate the blood pressure of a target area based on the difference in time between the peak of the PPG signal and the peak of a filtered pulse wave signal, as shown in FIG. 9C. Among blood pressure estimates, the maximum blood pressure estimate may be determined as a systolic blood pressure, and the minimum blood pressure estimate may be determined as a diastolic blood pressure. In addition, other blood pressures such as an average blood pressure may be estimated using the blood pressure estimates.

In order to measure blood pressure accurately, it is preferable that more light is received by the light-receiving pixel APX. As a considerable amount of light emitted from the display pixels (NPX and BPX) is absorbed by the peripheral tissues, the amount of light received by the light-receiving pixel APX may account for only a portion of the amount of light emitted from the display pixels (NPX and BPX). Thus, it may be difficult to precisely measure blood pressure based only on the amount of light received by the light-receiving pixel APX because of a low signal-to-noise ratio (SNR). However, due to the provision of the boost display pixel BPX, which is disposed near the light-receiving pixel APX and has a relatively high luminance, a relatively considerable amount of light can be provided as a source for blood pressure measurement. Accordingly, the SNR of the light-receiving pixel APX can be improved, and as a result, the precision of blood pressure measurement can be improved.

Referring to FIG. 8, reference numeral 122 denotes an area where the light-emitting layer and the light-receiving layer are positioned.

Figure 10:
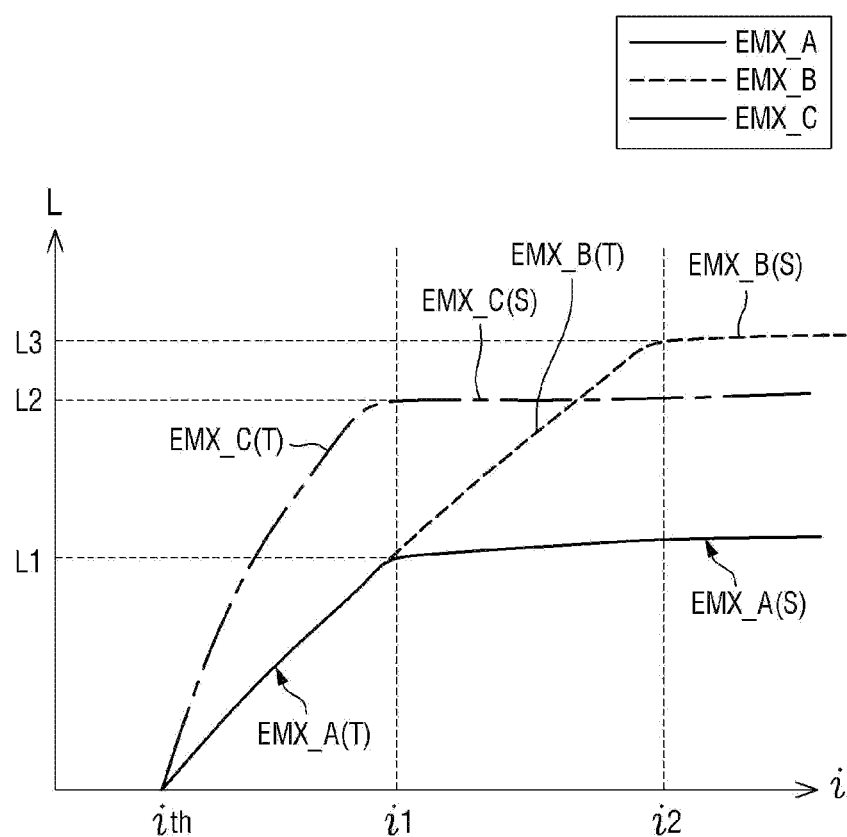
FIG. 10 is a graph showing the variation of the luminances of various display pixels against the amount of current.

FIG. 10 is a graph showing the variation of the luminances of various display pixels against the amount of current.

A boost display pixel BPX is distinguished from a normal display pixel NPX in that it has a much higher maximum luminance than a normal display pixel NPX. The luminance of a display pixel is generally proportional to the amount of current flowing in the light-emitting layer.

Referring to FIG. 10, the emission luminance curve of a display pixel may include a transition period T and a saturation period S. The display pixel may have a predetermined threshold current ith, and when a current starts to flow beyond the threshold current ith, the display pixel enters the transition period T when the amount of emission of the display pixel increases in accordance with the amount of current i. When the amount of current I reaches a maximum effective amount of current, the display pixel enters the saturation period S when the emission luminance of the display pixel does not significantly increase. During the saturation period S, the display pixel may have a theoretical maximum emission luminance.

The magnitude of the threshold current ith, the slope of the display pixel during the transition period T, the maximum effective amount of current, and/or the theoretical maximum emission luminance of the display pixel may vary depending on the type of light-emitting material or the area of the display pixel.

FIG. 10 illustrates an example in which emission pixels A, B, and C all have the same threshold current ith. Referring to FIG. 10, the emission pixel A ("EMX_A") has a slope m1 (where m1 is a positive number) during a transition period EMX_A(T), and at a current amounti1, the emission pixel A enters a saturation period EMX_A(S) and has a maximum luminance L1. The emission pixel B ("EMX_B") has the slope m1 during a transition period EMX_B(T), and at a current amounti2 (where i2>i1), the emission pixel B enters a saturation period EMX_B(S) and has a maximum luminance L3 (where L3>L1). The emission pixel C ("EMX_C") has a slope m2 (where m2>m1) during a transition period EMX_C(T), and at the current amount i1, the emission pixel C enters a saturation period EMX_C(S) and has a maximum luminance L2 (where L3>L2>L1).

By using these emission pixels having different luminance versus current values, a boost display pixel BPX having a higher maximum emission luminance than a normal display pixel NPX can be realized. For example, the emission pixel A ("EMX_A") may be applied as a normal display pixel NPX, and the emission pixel B or C ("EMX_B" or "EMX_C") may be applied as the boost display pixel BPX, thereby designing a boost display pixel BPX having a higher maximum emission luminance than a normal display pixel NPX. In another example, the emission pixel C may be applied as a normal display pixel NPX, and the emission pixel B, which has a higher maximum luminance than the emission pixel C, may be applied as a boost display pixel BPX.

Alternatively, an emission pixel not necessarily having a high theoretical maximum emission luminance may be applied as a boost display pixel BPX. For example, the emission pixel A ("EMX_A") may be applied as both a normal display pixel NPX and a boost display pixel BPX, and different pixel circuits CUI may be applied to the normal display pixel NPX and the boost display pixel BPX such that a maximum current amount applied to the boost display pixel BPX may become greater than a maximum current amount applied to the normal display pixel NPX. In this example, the actual maximum luminance of the boost display pixel BPX can be controlled to be higher than the actual maximum luminance of the normal display pixels NPX. Similarly, the emission pixel B ("EMX_B") or C ("EMX_C"), which has a relatively high theoretical maximum emission luminance, may be applied as a normal display pixel NPX, and the emission pixel A may be applied as a boost display pixel BPX. Even in this case, the maximum luminance of the boost display pixel BPX may be set to be higher than the maximum luminance of the normal display pixel NPX by controlling the maximum amount of current to be applied, differently with pixel circuits CUI.

Increasing the maximum luminances of the display pixels (NPX and BPX) may result in increases in power consumption and the amount of heat generated. However, in a case where the maximum luminance of only the boost display pixel BPX is selectively raised, increases in power consumption and the amount of heat generated can be suppressed, as compared to a case where the maximum luminances of all the display pixels (NPX and BPX) are raised.

In addition, as the boost display pixel BPX is disposed near the light-receiving pixel APX, the number of boost display pixels BPX is less than the number of normal display pixels NPX. Thus, although the maximum luminance of the boost display pixel BPX is raised, increases in power consumption and the amount of heat generated can be appropriately limited. In a case where the maximum luminance of the normal display pixels NPX is raised, intrinsic colors displayed by the normal display pixels NPX may undesirably change. On the contrary, in a case where the maximum luminance of only the boost display pixel BPX is selectively raised, the degradation of image quality can be minimized, even if the boost display pixel BPX is used to form a display screen, because the boost display pixel BPX accounts for only a portion of the entire display area.

The maximum luminance of the boost display pixel BPX may be about 1.5 to 10 times the maximum luminance of the normal display pixels NPX. Here, the normal display pixels NPX may be the red and green normal display pixels NPX_R and NPX_G. If the maximum luminance of the boost display pixel BPX is about 1.5 times or greater the maximum luminance of the normal display pixels NPX, the SNR of the light-receiving pixel APX can be improved. The maximum luminance of the boost display pixel BPX may be controlled to be about 10 times or less the maximum luminance of the normal display pixels NPX in consideration of power consumption and the visibility of the boost display pixel BPX.

The normal display pixels NPX emit light at a range of luminances up to their maximum luminance depending on data applied thereto. The boost display pixel BPX may also emit light at a range of luminances up to its maximum luminance and may emit light at its maximum luminance to raise the SNR of the light-receiving pixel APX during a blood pressure measurement mode. Thus, during the blood pressure measurement mode, the boost display pixel BPX may have at least about 10 times as high a luminance as the normal display pixels NPX.

There are factors that determine the maximum luminance of each display pixel such as emission area, emission volume, a driving current, and emission efficiency. The boost display pixel BPX, which has a relatively high maximum luminance, may have a larger emission area than the normal display pixels NPX, include a thicker light-emitting layer than the normal display pixels NPX, have a higher driving current than the normal display pixels NPX, or include a light-emitting layer with a higher emission efficiency than the normal display pixels NPX. Various embodiments for allowing the boost display pixel BPX to have a relatively high maximum luminance will hereinafter be described.

The layout of the normal display pixels NPX, the boost display pixel BPX, and the light-receiving pixel APX will hereinafter be described.

Figure 11:
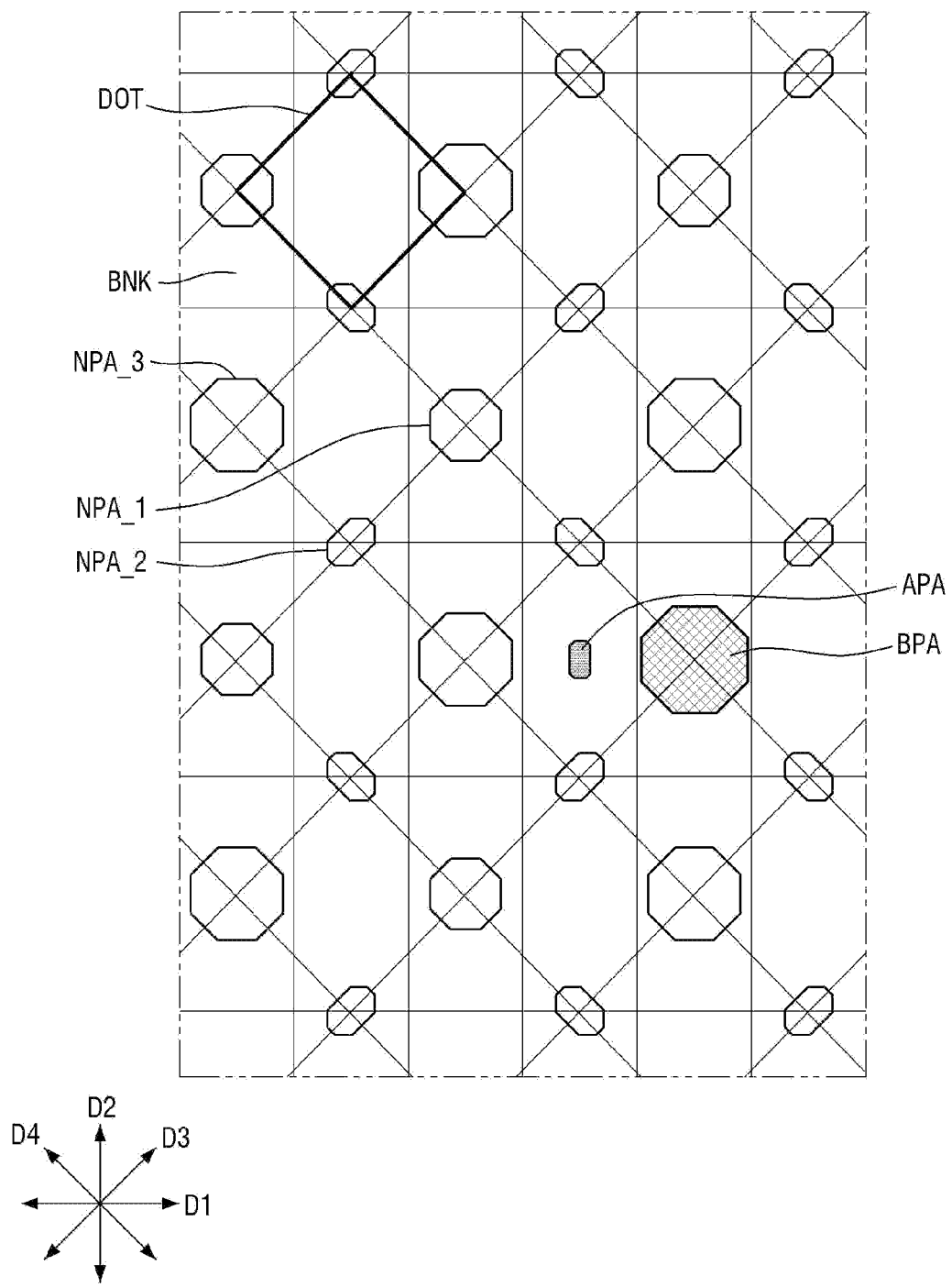
FIG. 11 is a layout view of pixels of a display layer according to an embodiment of the present disclosure.

FIG. 11 is a layout view of pixels of a display layer according to an embodiment of the present disclosure.

FIG. 11 illustrates the layout of the active areas of normal display pixels NPX, a boost display pixel BPX, and a light-receiving pixel APX. Here, the active areas of the normal display pixels NPX and the boost display pixel BPX may be light-emitting areas of a light-emitting layer that are exposed by openings of a bank layer BNK, and the active area of the light-receiving pixel APX may be a light-emitting area of a photoelectric conversion layer that is exposed by an opening of the bank layer BNK.

Referring to FIG. 11, the normal display pixels NPX may include first normal display pixels NPX_R, second normal display pixels NPX_G, and third normal display pixels NPX_B. Here, the first normal display pixels NPX_R may be, but are not limited to, red normal display pixels that emit red light having a main wavelength of about 600 nm to about 750 nm, the second normal display pixels NPX_G may be, but are not limited to, green normal display pixels that emit green light having a main wavelength of about 480 nm to about 560 nm, and the third normal display pixels NPX_B may be, but are not limited to, blue normal display pixels that emit blue light having a main wavelength of about 370 nm to about 460 nm. The boost display pixel BPX may be a red boost display pixel that emits red light, like the first normal display pixels NPX_R with the same range of wavelengths, but the present disclosure is not limited thereto.

For convenience, the active areas of the first normal display pixels NPX_R will hereinafter be referred to as first normal active areas NPA_1, the active areas of the second normal display pixels NPX_G will hereinafter be referred to as second normal active areas NPA_2, the active areas of the third normal display pixels NPX_B will hereinafter be referred to as third normal active areas NPA_3, the active area of the boost display pixel BPX will hereinafter be referred to as a boost active area BPA, and the active area of the light-receiving pixel APX will hereinafter be referred to as a light-receiving active area APA.

Each of the first normal active areas NPA_1 may be larger than each of the second normal active areas NPA_2, and may be smaller than each of the third normal active areas NPA_3. The boost active area BPA may be larger than each of the first normal active areas NPA_1, which emit light of the same color as the boost active area BPA, and each of the third normal active areas NPA_3, which are the largest active areas among the active areas of the normal display pixels NPX.

Each of the first normal active areas NPA_1 and each of the third normal active areas NPA_3 may generally have an octagonal shape and may be alternately arranged in a row direction (or a first direction D1). Each of the second normal active areas NPA_2 may generally have an octagonal or hexagonal shape and may be arranged in the first direction D1. Rows where the first normal active areas NPA_1 and the third normal active areas NPA_3 are alternately arranged and rows where the second normal active areas NPA_2 are arranged are alternately arranged in a column direction (or a second direction D2).

The first normal active areas NPA_1 and the third normal active areas NPA_3 may be alternately arranged in the second direction D2. The second normal active areas NPA_2 may be disposed between the first normal active areas NPA_1 and the third normal active areas NPA_3. The number of second normal active areas NPA_2 may be twice the number of third normal active areas NPA_3 in a unit area (i.e., DOT), but the present disclosure is not limited thereto. The second normal active areas NPA_2 may be classified into first-type second normal active areas NPA_2 that are longer in a second diagonal direction (or a fourth direction D4) than in a first diagonal direction (or a third direction D3) and second-type second normal active areas NPA_2 that are longer in the fourth direction D4 than in the third direction D3, and the first-type second normal active areas NPA_2 and the second-type second normal active areas NPA_2 may be alternately arranged in the first and second directions D1 and D2.

Each of dots "DOT", which are minimal units that form an image and are capable of displaying a color, may be defined by one first normal active area NPA_1, one third normal active area NPA_3, and two adjacent second normal active areas NPA_2 and may have a rhombus shape obtained by connecting the centers of the first normal active area NPA_1, the third normal active area NPA_3, and the two adjacent second normal active areas NPA_2. Each of a plurality of display active areas (NPA_1, NPA_2, and NPA_3) may be shared by four adjacent dots "DOT".

The light-receiving area APA may be disposed between the display active areas (NPA_1, NPA_2, and NPA_3). For example, the light-receiving area APA may be disposed at the intersection between a row where the first normal active area NPA_1 and the third normal active area NPA_3 are adjacent with each other in the first direction D1, and a column where two adjacent second normal active areas NPA_2 are arranged in the second direction D2.

The boost active area BPA may be disposed at the location of a first normal active area NPA_1 to replace the first normal active area NPA_1. For example, the boost active area BPA may be disposed at the location of a first normal active area NPA_1 closest to the light-receiving active area APA in the first direction D1. In another example, not only the first normal active area NPA_1 closest to the light-receiving area APA, but also other first normal active areas NPA_1 around the light-receiving area APA may be replaced with boost active areas BPA.

As one or more boost active areas BPA are provided to replace as many first normal active areas NPA_1, the number of first normal active areas NPA_1 may be reduced by as much as the number of boost active areas BPA. If the number of first normal active areas NPA_1 and the number of third normal active areas NPA_3 are identical in a display area having no boost active areas BPA, the sum of the number of first normal active areas NPA_1 and the number of boost active areas BPA may be identical to the number of third normal active areas NPA_3 in a display area having boost active areas BPA.

In a display mode, the boost active area(s) BPA, like the first normal active areas NPA_1, may emit light of various gradations of red to configure a display screen. In a blood pressure measurement mode, the boost active area(s) BPA may emit light at its maximum luminance regardless of the gray level of its neighboring display active areas.

FIG. 11 illustrates an example in which the boost active area(s) BPA and the first normal active areas NPA_1 both emit light of the same color, but the present disclosure is not limited thereto. Alternatively, a plurality of boost active areas BPA may be provided, and some or all of the plurality of boost active areas BPA may emit light of the same color as the second normal active areas NPA_2. In this case, two adjacent second normal active areas NPA_2 adjacent to the light-receiving active area APA in the second direction D2 may be replaced with boost active areas BPA and their respective neighboring second normal active areas NPA_2 may also be replaced with boost active areas BPA.

The boost active area(s) BPA are arranged at similar locations to the display active areas (NPA_1, NPA_2, and NPA_3) and have a higher maximum luminance than the display active areas (NPA_1, NPA_2, and NPA_3). It will hereinafter be described how to selectively achieve a high maximum luminance with a boost active area BPA with reference to FIGS. 12, 13, 14, 15, 16, and 17.

Figure 12:
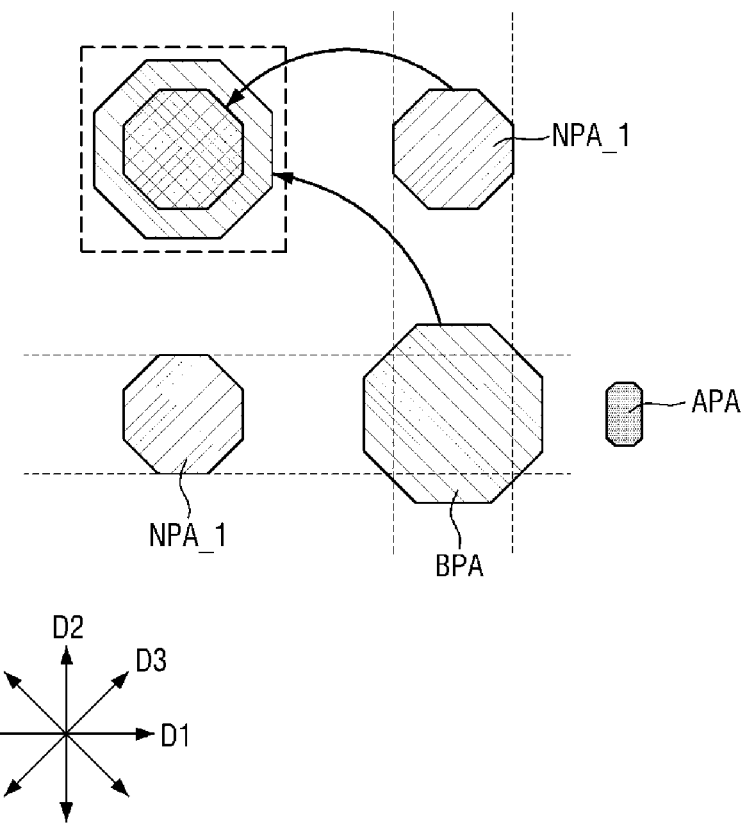
FIG. 12 is a schematic plan view comparing the shapes of first normal active areas and a boost active area according to an embodiment of the present disclosure.

FIG. 12 is a schematic plan view comparing the shapes of first normal active areas and a boost active area according to an embodiment of the present disclosure and illustrates the shape of a first normal active area and the boost active area as laid over each other.

Referring to FIG. 12, a boost active area BPA adjacent to a light-receiving active area APA may have a larger size than each of first normal active areas NPA_1. The larger the active area, the larger the effective emission area, and the higher the maximum luminance. Thus, although the light-emitting layers of the boost active area BPA and the first normal active areas NPA_1 are formed of the same material and have the same thickness, the maximum luminance of the boost active area BPA may be higher than the maximum luminance of the first normal active areas NPA_1. The maximum luminance of the boost active area BPA may be twice the maximum luminance of the first normal active areas NPA_1, and the size of the boost active area BPA may be set to be twice the size of the first normal active areas NPA_1.

The boost active area BPA may have substantially the same shape as the first normal active areas NPA_1 in a plan view and may be a similar figure to the first normal active areas NPA_1. The boost active area BPA may be larger than the first normal active areas NPA_1 in both the first and second directions D1 and D2, and the differences in length in the first and second directions D1 and D2 between the boost active area BPA and the first normal active areas NPA_1 may be substantially the same. However, the present disclosure is not limited to this. Alternatively, the boost active area BPA may have a larger size than, but a different planar shape from, the first normal active areas NPA_1.

Figure 13:
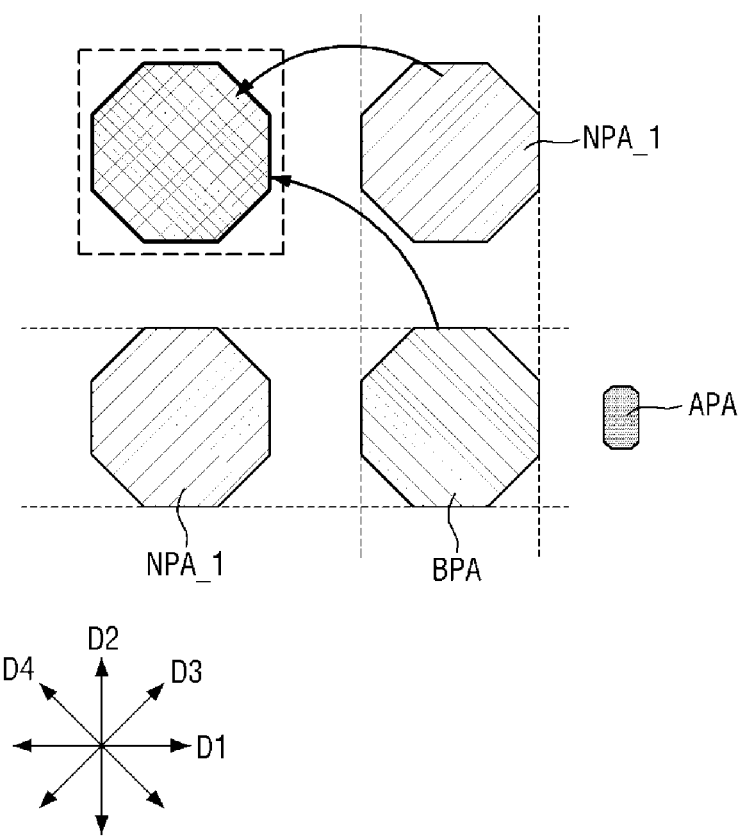
FIG. 13 is a schematic plan view comparing the shapes of first normal active areas and a boost active area according to another embodiment of the present disclosure.

FIG. 13 is a schematic plan view comparing the shapes of first normal active areas and a boost active area according to another embodiment of the present disclosure.

FIG. 13 illustrates an example in which first normal active areas NPA_1 have substantially the same size and shape as a boost active area BPA. According to the embodiment of FIG. 13, as the emission efficiency of a light-emitting layer of the boost active area BPA is greater than the emission efficiency of light-emitting layers of the first normal active areas NPA_1, the boost active area BPA can achieve a higher maximum luminance than the first normal active areas NPA_1.

Specifically, a light-emitting material has its own emission efficiency. The emission efficiency of one light-emitting material may be lower than the emission efficiency of another light-emitting material. In other words, the slope of an emission luminance curve of one light-emitting material may be less than the slope of an emission luminance curve of another light-emitting material during a transition period. In addition, some light-emitting materials may have more accurate color reproducibility than other light-emitting materials. If a light-emitting material A has a relatively low emission efficiency but is suitable for realizing excellent color reproducibility and a light-emitting material B has twice as high an emission efficiency as the light-emitting material A but has poor color reproducibility, the light-emitting material A may be applied to the light-emitting layers of the first normal active areas NPA_1 to provide an excellent image quality, and the light-emitting material B may be applied to the light-emitting layer of the boost active area BPA so that the boost active area BPA may have twice as high a maximum luminance as the first normal active areas NPA_1.

Figure 14:
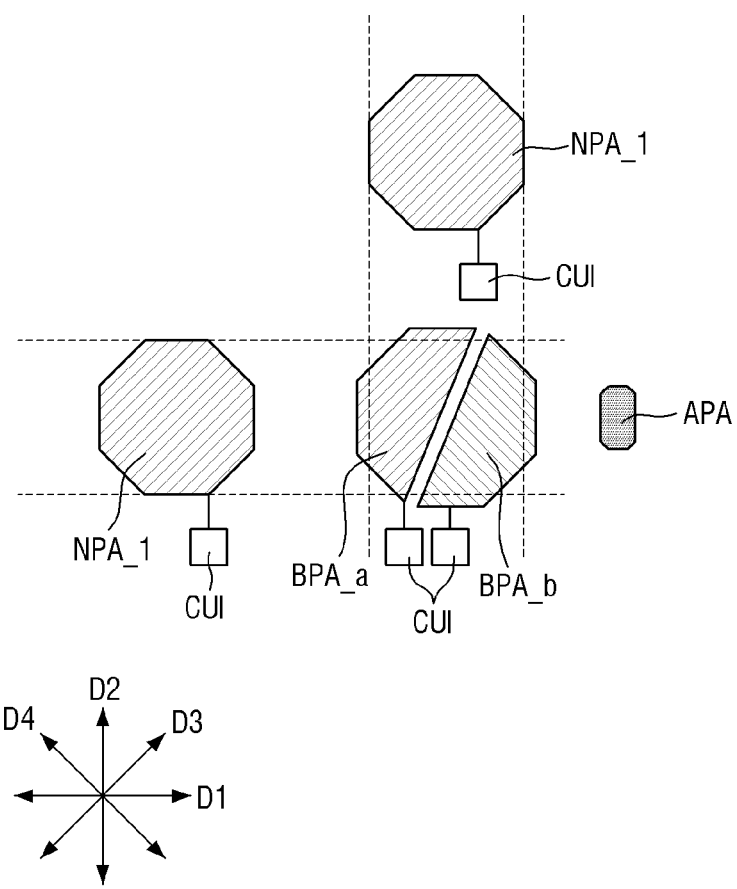
FIG. 14 is a schematic plan view comparing the shapes of first normal active areas and a boost active area according to another embodiment of the present disclosure.

FIG. 14 is a schematic plan view comparing the shapes of first normal active areas and a boost active area according to another embodiment of the present disclosure.

FIG. 14 illustrates an example in which a boost active area BPA is divided into a plurality of subareas (BPA_a and BPA_b) that can be driven separately. Referring to FIG. 14, the boost active area BPA may include first and second subareas BPA_a and BPA_b, which are adjacent to each other. The light-emitting material A of FIG. 13, which has relatively low emission efficiency, may be applied to the first subarea BPA_a, and the light-emitting material B of FIG. 13, which has relatively high emission efficiency, may be applied to the second subarea BPA_b. The first and second subareas BPA_a and BPA_b may be driven separately by separate pixel circuits CUI. The maximum luminance of the boost active area BPA may be the sum of the maximum luminances of the first and second subareas BPA_a and BPA_b.

The boost active area BPA, which includes the first and second subareas BPA_a and BPA_b, can satisfy all the conditions required for both a display mode and a blood pressure measurement mode. For example, the amount of light incident upon a light-receiving active area APA can be raised by driving the first subarea BPA_a, which is suitable for color reproducibility, mainly during the display module and driving the second subarea BPA_b to emit light at its maximum luminance during the blood pressure measurement mode.

Figure 15:
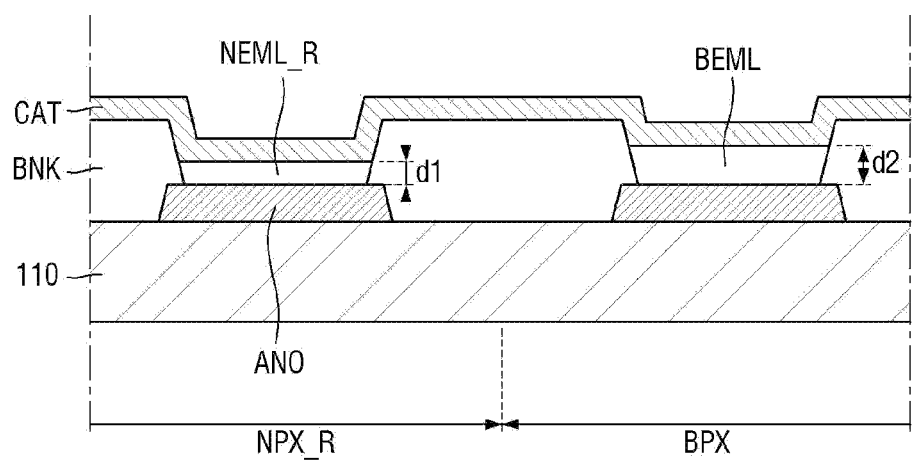
FIG. 15 is a schematic cross-sectional view comparing the shapes of a first normal display pixel and a boost display pixel according to an embodiment of the present disclosure.

FIG. 15 is a schematic cross-sectional view comparing the shapes of a first normal display pixel and a boost display pixel according to an embodiment of the present disclosure.

FIG. 15 illustrates an example in which a thickness d2 of a light-emitting layer of a boost display pixel BPX is greater than a thickness d1 of a light-emitting layer of a first normal display pixel NPX_R. Referring to FIG. 15, as the thickness d2 of the light-emitting layer of the boost display pixel BPX is greater than the thickness d1 of the light-emitting layer of the first normal display pixel NPX_R, the boost display pixel BPX may have greater emission volume than the first normal display pixel NPX_R and may thus have higher maximum luminance than the first normal display pixel NPX_R. Accordingly, although the active areas of the boost display pixel BPX and the first normal display pixel NPX_R have the same size in a plan view and the light-emitting layers of the boost display pixel BPX and the first normal display pixel NPX_R are formed of the same material, the boost display pixel BPX can have higher maximum luminance than the first normal display pixel NPX_R.

Figure 16:
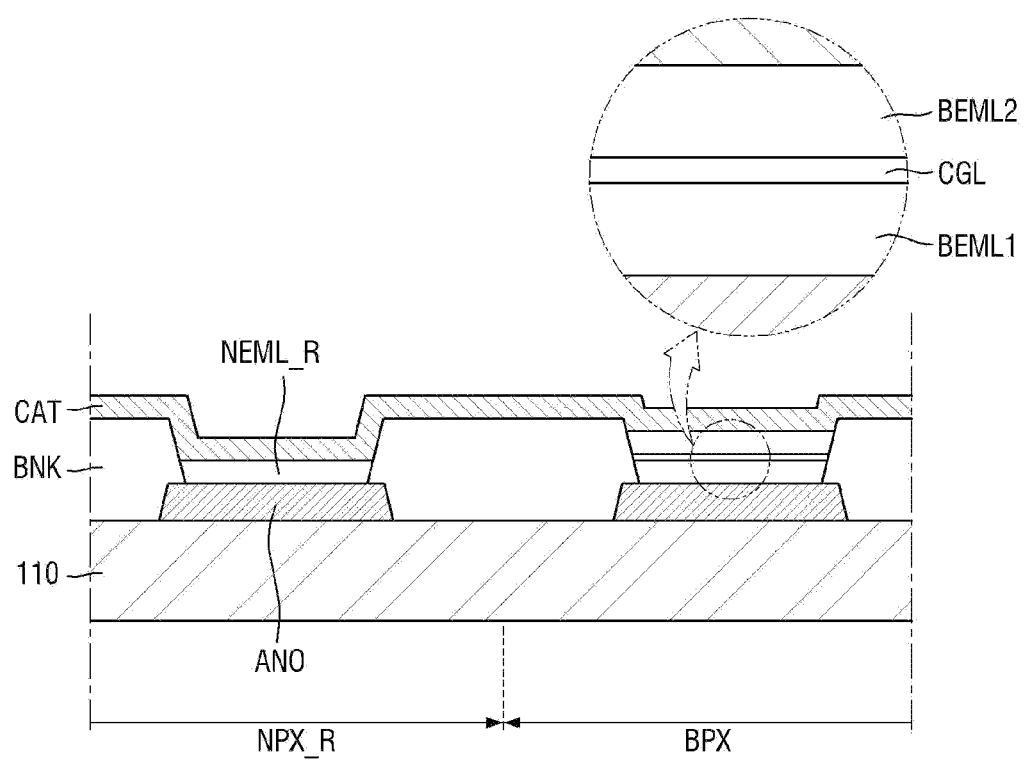
FIG. 16 is a schematic cross-sectional view comparing the shapes of a first normal display pixel and a boost display pixel according to another embodiment of the present disclosure.

FIG. 16 is a schematic cross-sectional view comparing the shapes of a first normal display pixel and a boost display pixel according to another embodiment of the present disclosure.

Referring to FIG. 16, a boost display pixel BPX may include a plurality of first and second light-emitting layers BEML1 and BEML2, which are stacked. A layer that assists with the transfer of charge between the first and second light-emitting layers BEML1 and BEML2, for example, a charge generation layer CGL, may be interposed between the first and second light-emitting layers BEML1 and BEML2, but the present disclosure is not limited thereto. As the first and second light-emitting layers BEML1 and BEML2 both contribute to the emission of light, the maximum luminance of the boost display pixel BPX may increase, as compared to a case where the boost display pixel BPX includes only one light-emitting layer. For example, although the first and second light-emitting layers BEML1 and BEML2 have the same material and the same volume as a light-emitting layer of a first normal display pixel NPX_R, the boost display pixel BPX may have twice as high a maximum luminance as the first normal display pixel NPX_R. The first light-emitting layer BEML1 may include the light-emitting material A of FIG. 13, and the second light-emitting layer BEML2 may include the light-emitting material B of FIG. 13.

Figure 17:
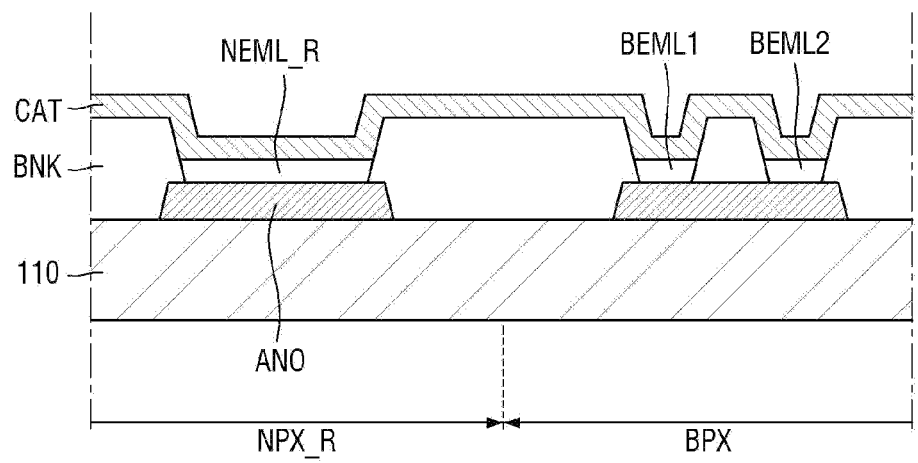
FIG. 17 is a schematic cross-sectional view comparing the shapes of a first normal display pixel and a boost display pixel according to another embodiment of the present disclosure.

FIG. 17 is a schematic cross-sectional view comparing the shapes of a first normal display pixel and a boost display pixel according to another embodiment of the present disclosure.

The embodiment of FIG. 17 differs from the embodiment of FIG. 16 in that a plurality of first and second light-emitting layers BEML1 and BEML2 of a boost display pixel BPX are separated from each other over a first electrode ANO by a bank layer BNK. The embodiment of FIG. 17 differs from the embodiment of FIG. 14 in that the first and second light-emitting layers BEML1 and BEML2 are disposed on the same first electrode ANO.

According to the embodiment of FIG. 17, as the first and second light-emitting layers BEML1 and BEML2 both contribute to the emission of light, the maximum luminance of the boost display pixel BPX can be set to be higher than the maximum luminance of a first normal display pixel NPX_R by controlling the sizes and the types of light-emitting materials of the first and second light-emitting layers BEML1 and BEML2.

Figure 18:
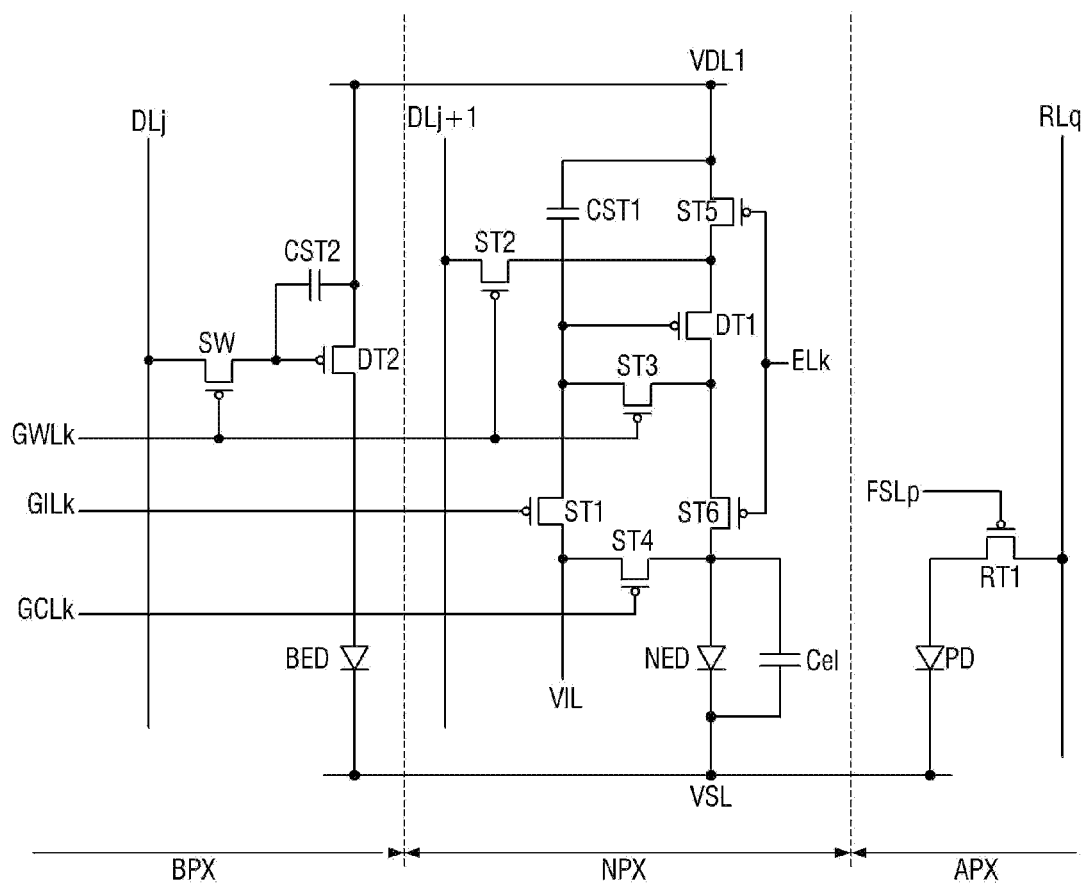
FIG. 18 is a circuit diagram illustrating a normal display pixel, a boost display pixel and a light-receiving circuit of a display device according to an embodiment of the present disclosure.

FIG. 18 is a circuit diagram illustrating a normal display pixel, a boost display pixel and a light-receiving circuit of a display device according to an embodiment of the present disclosure. Pixel circuitry of a display device will hereinafter be described with reference to FIG. 18.

Referring to FIG. 18, a normal display pixel NPX may be connected to a k-th display initialization line GILk, a k-th display write line GWLk, and a k-th display control line GCLk (where k is a positive integer). In addition, the normal display pixel NPX may be connected to a first voltage line VDL1, to which a first driving voltage is supplied, a reference voltage line VSL, to which a ground voltage or a reference voltage lower than the first driving voltage is supplied, and an initialization voltage line VIL, to which an initialization voltage is supplied.

The normal display pixel NPX may include a normal display pixel circuitry and a boost display pixel circuitry. The normal display pixel circuitry may include a driving transistor DT1, switching elements, and a capacitor CST. The switching elements may include first through sixth transistors ST1, ST2, ST3, ST4, ST5, and ST6. The boost display pixel circuitry may include a driving transistor DT2, a switching transistor SW, and a capacitor CST2.

The driving transistor DT1 may include a gate electrode, a first electrode, and a second electrode. The driving transistor DT1 controls a drain-source current or a driving current Ids in accordance with a data voltage applied to the gate electrode. The driving current Ids, which flows through the channel of the driving transistor DT1, may be proportional to the square of the difference between a threshold voltage Vth and a voltage Vgs, which is the voltage between the first electrode and the gate electrode of the driving transistor DT1, as indicated by Equation (1):

$$Ids = k' \times (Vgs - Vth)^2$$

where k' is a proportionality coefficient determined by the structure and physical characteristics of the driving transistor DT1, Vgs is the voltage between the first electrode and the gate electrode of the driving transistor DT1, and Vth is the threshold voltage of the driving transistor DT1.

A normal light-emitting element NED emits light in accordance with the driving current Ids. The greater the driving current Ids, the greater the amount of light emitted by the normal light-emitting element NED.

The normal light-emitting element NED may be an OLED including an organic light-emitting layer disposed between the anode and the cathode thereof. Alternatively, the normal light-emitting element NED may be an inorganic light-emitting element including an inorganic semiconductor disposed between the anode and the cathode thereof. Alternatively, the normal light-emitting element NED may be a quantum-dot light-emitting element including a quantum-dot light-emitting layer disposed between the anode and the cathode thereof. Alternatively, the normal light-emitting element NED may be a micro-light-emitting element including a microLED disposed between the anode and the cathode thereof.

The anode of the normal light-emitting element NED may be connected to the first electrode of the fourth transistor ST4 and the second electrode of the sixth transistor ST6, and the cathode of the normal light-emitting element NED may be connected to the reference voltage line VSL. A parasitic capacitor Cel may be formed between the anode and the cathode of the normal light-emitting element NED.

The first transistor ST1 is turned on by an initialization scan signal from the k-th display initialization line GILk to connect the gate electrode of the driving transistor DT1 to the initialization voltage line VIL. Accordingly, an initialization voltage from the initialization voltage line VIL may be applied to the gate electrode of the driving transistor DT1. The gate electrode of the first transistor ST1 may be connected to the k-th display initialization line GILk, the first electrode of the first transistor ST1 may be connected to the gate electrode of the driving transistor DT1, and the second electrode of the first transistor ST1 may be connected to the initialization voltage line VIL.

The second transistor ST2 is turned on by a display write signal from the k-th display write line GWLk to connect the first electrode of the driving transistor DT1 to a (j+1)-th data line DLj+1. As a result, a data voltage from the (j+1)-th data line DLj+1 may be applied to the first electrode of the driving transistor DT1. The gate electrode of the second transistor ST2 may be connected to the k-th display write line GWLk, the first electrode of the second transistor ST2 may be connected to the first electrode of the driving transistor DT1, and the second electrode of the second transistor ST2 may be connected to the (j+1)-th data line DLj+1.

The third transistor ST3 is turned on by the display write signal from the k-th display write line GWLk to connect the gate electrode and the second electrode of the driving transistor DT1. As a result, the driving transistor DT1 may operate as a diode. The gate electrode of the third transistor ST3 may be connected to the k-th display write line GWLk, the first electrode of the third transistor ST3 may be connected to the second electrode of the driving transistor DT1, and the second electrode of the third transistor ST3 may be connected to the gate electrode of the driving transistor DT1.

The fourth transistor ST4 is turned on by a display control signal from the k-th display control line GCLk to connect the anode of the normal light-emitting element NED to the initialization voltage line VIL. The initialization voltage from the initialization voltage line VIL may be applied to the anode of the normal light-emitting element NED. The gate electrode of the fourth transistor ST4 may be connected to the k-th display control line GCLk, the first electrode of the fourth transistor ST4 may be connected to the anode of the normal light-emitting element NED, and the second electrode of the fourth transistor ST4 may be connected to the initialization voltage line VIL.

The fifth transistor ST5 is turned on by an emission signal from the k-th emission line Elk to connect the first electrode of the driving transistor DT1 to the first driving voltage line VDL. The gate electrode of the fifth transistor ST5 may be connected to the k-th emission line Elk, the first electrode of the fifth transistor ST5 may be connected to the first driving voltage line VDL, and the second electrode of the fifth transistor ST5 may be connected to the first electrode of the driving transistor DT1.

The sixth transistor ST6 is disposed between the second electrode of the driving transistor DT1 and the anode of the normal light-emitting element NED. The sixth transistor ST6 may be turned on by an emission control signal from the k-th emission line Elk to connect the second electrode of the driving transistor DT1 to the anode of the normal light-emitting element NED. The gate electrode of the sixth transistor ST6 may be connected to the k-th emission line ELk, the first electrode of the sixth transistor ST6 may be connected to the second electrode of the driving transistor DT1, and the second electrode of the sixth transistor ST6 may be connected to the anode of the normal light-emitting element NED.

When the fifth and sixth transistors ST5 and ST6 are both turned on, the driving current Ids of the driving transistor DT1 may flow to the normal light-emitting element NED in accordance with the data voltage applied to the driving transistor DT1.

A capacitor CST1 is formed between the gate electrode of the driving transistor DT1 and the first driving voltage line VDL. The first capacitor electrode of the capacitor CST1 may be connected to the gate electrode of the driving transistor DT1, and the second capacitor electrode of the capacitor CST1 may be connected to the first driving voltage line VDL.

If the first electrodes of the first through sixth transistors ST1 through ST6 and the driving transistor DT1 are source electrodes, the second electrodes of the first through sixth transistors ST1 through ST6 and the driving transistor DT1 may be drain electrodes. Alternatively, if the first electrodes of the first through sixth transistors ST1 through ST6 and the driving transistor DT1 are drain electrodes, the second electrodes of the first through sixth transistors ST1 through ST6 and the driving transistor DT1 may be source electrodes.

The active layers of the first through sixth transistors ST1, ST2, ST3, ST4, ST5, and ST6 and the driving transistor DT1 may be formed of one of polysilicon, amorphous silicon, and an oxide semiconductor. FIG. 6 illustrates that the first through sixth transistors ST1, ST2, ST3, ST4, ST5, and ST6 and the driving transistor DT1 are formed as P-type metal-oxide semiconductor field-effect transistors (MOSFETs), but the present disclosure is not limited thereto. Alternatively, the first through sixth transistors ST1, ST2, ST3, ST4, ST5, and ST6 and the driving transistor DT1 may be formed as N-type MOSFETs. Yet alternatively, at least one of the first through sixth transistors ST1, ST2, ST3, ST4, ST5, and ST6 may be formed as an N-type MOSFET.

The boost display pixel BPX may have the same pixel configuration as the normal display pixel NPX. For example, the boost display pixel BPX may have pixel circuitry with a "7T1C" (7 transistors and 1 capacitor) configuration. However, in a case where the boost display pixel BPX is driven at its maximum gray level to emit light at its maximum luminance, the boost display pixel BPX may have a simpler pixel circuitry than the normal display pixel NPX. For example, the boost display pixel BPX may include fewer transistors than the normal display pixel NPX. When the boost display pixel BPX has a simplified pixel circuitry, the use of space for a circuit layer can be improved, and as a result, the boost display pixel BPX can respond properly to high resolution. The boost display pixel BPX of FIG. 18 has pixel circuitry with a "2T1C" (2 transistors and 1 capacitor) configuration.

As illustrated in FIG. 18, the boost display pixel BPX may be connected to the k-th display write line GWLk, the first voltage line VDL, to which the first driving voltage is supplied, and the reference voltage line VSL, to which the ground voltage or the reference voltage lower than the first driving voltage is supplied.

A driving transistor DT2 is connected between the first voltage line VDL1 and the anode of a boost light-emitting element BED and controls a driving current flowing in the boost light-emitting element BED. The cathode of the boost light-emitting element BED is connected to the reference voltage line VSL. A switching transistor SW is turned on by the display write signal from the k-th display write line GWLk to connect the gate electrode of the driving transistor DT2 to the (j+1)-th data line DLj+1. A capacitor CST2 is connected between the first electrode and the gate electrode of the driving transistor DT2.

A light-receiving pixel APX may be connected to a p-th sensing scan line FSLp (where p is a positive integer) and a q-th sensing line RLq (where q is a positive integer). The light-receiving pixel APX may be additionally connected to the reference voltage line VSL.

The light-receiving pixel APX may include a sensing transistor RT1 and a light-receiving element PD.

The light-receiving element PD may be a photodiode including an anode, a photoelectric conversion layer, and a cathode. The anode of the light-receiving element PD may be connected to the first electrode of the first sensing transistor RT1, and the cathode of the light-receiving element PD may be connected to the reference voltage line VSL.

The first sensing transistor RT1 is turned on by a scan signal from the p-th sensing scan line FSLp to connect the sensing anode of the light-receiving element PD to the q-th sensing line RLq. As a result, a voltage from the sensing anode of the light-receiving element PD may be applied to the q-th sensing line RLq. The gate electrode of the first sensing transistor RT1 may be connected to the p-th sensing scan line FSLp, the first electrode of the first sensing transistor RT1 may be connected to the sensing anode of the light-receiving element PD, and the second electrode of the first sensing transistor RT1 may be connected to the q-th sensing line RLq.

As described above, the normal display pixel NPX, the boost display pixel BPX, and the light-receiving pixel APX share a considerable number of lines. Thus, the circuit structure of an entire display device can be simplified. Also, as the transistors and the diodes of each of the normal display pixel NPX, the boost display pixel BPX, and the light-receiving pixel APX are formed of materials that form the same layers, integration can be facilitated, and process efficiency can be improved.

In addition, as the boost display pixel BPX has its own distinctive pixel circuitry unlike the normal display pixel NPX, the boost display pixel BPX can emit light at its maximum luminance, regardless of the gray level of the normal display pixel NPX, during the blood pressure measurement mode.

Figure 19:
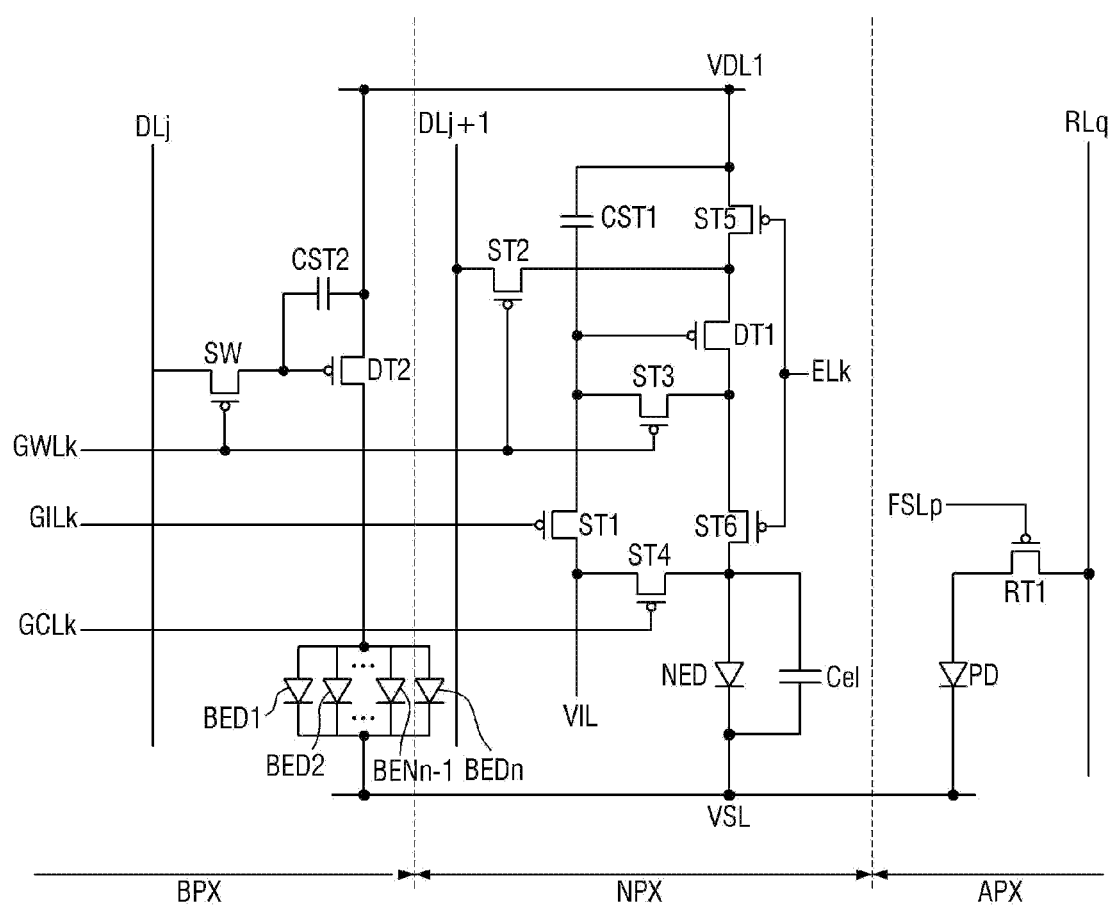
FIG. 19 is a circuit diagram illustrating a normal display pixel, a boost display pixel and a light-receiving circuit of a display device according to another embodiment of the present disclosure.

FIG. 19 is a circuit diagram illustrating a normal display pixel, a boost display pixel and a light-receiving circuit of a display device according to another embodiment of the present disclosure.

The embodiment of FIG. 19 differs from the embodiment of FIG. 18 in that a plurality of boost light-emitting elements (BED1, BED2, . . . , BEDn−1, and BEDn) of a boost display pixel BPX are connected to a single driving transistor DT2. The boost light-emitting elements (BED1, BED2, . . . , BEDn−1, and BEDn) are connected in parallel to one another. The boost light-emitting elements (BED1, BED2, . . . , BEDn−1, and BEDn) may be disposed in different boost display pixels BPX.

In a case where the boost light-emitting elements (BED1, BED2, . . . , BEDn−1, and BEDn) emit light at their maximum luminance for measuring blood pressure, emission data of the boost light-emitting elements (BED1, BED2, . . . , BEDn−1, and BEDn) may all be the same. Thus, there is substantially no difference between when a data signal is applied to each data line, to which a boost light-emitting element BED is connected, as illustrated in FIG. 18, and when a plurality of boost light-emitting elements BED are connected in parallel and a data signal is applied via one pixel circuit, as illustrated in FIG. 19. The embodiment of FIG. 19 can simplify pixel circuitry, reduce manufacturing cost, and increase the degree of integration.

Figure 20:
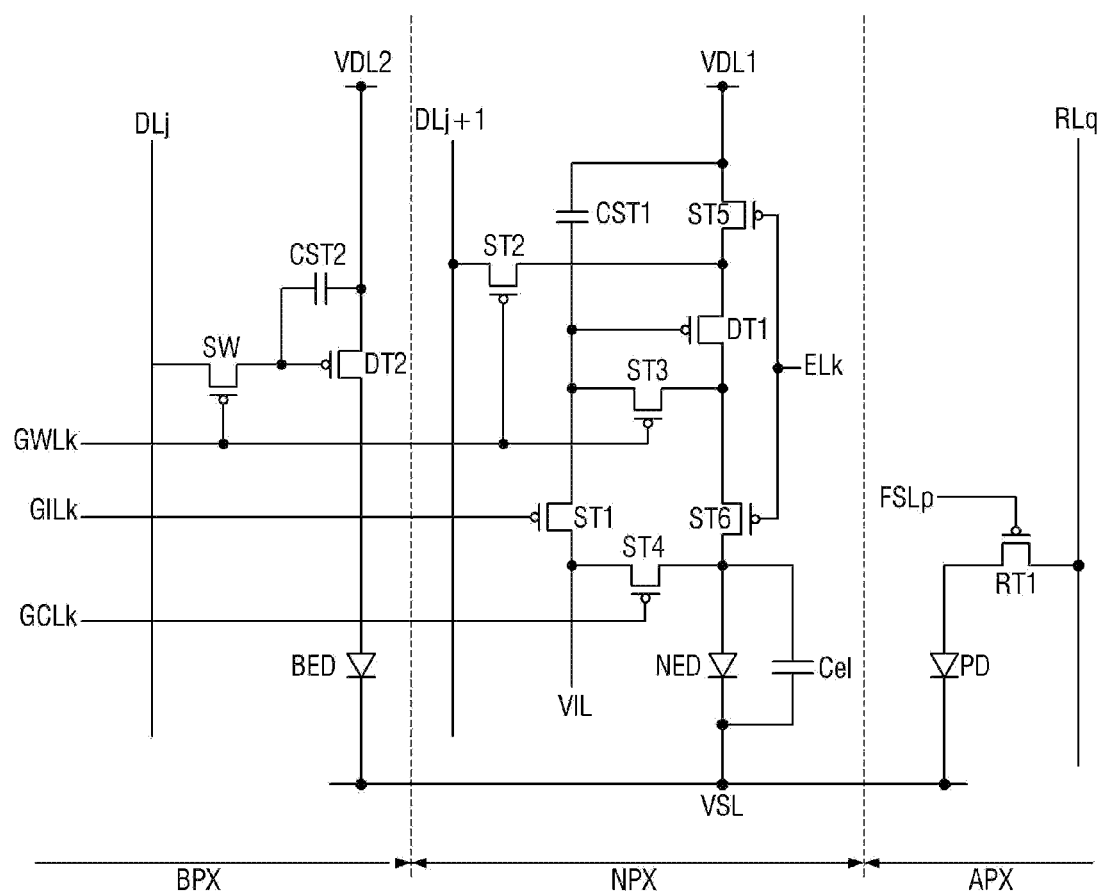
FIG. 20 is a circuit diagram illustrating a normal display pixel, a boost display pixel and a light-receiving circuit of a display device according to another embodiment of the present disclosure.

FIG. 20 is a circuit diagram illustrating a normal display pixel, a boost display pixel and a light-receiving circuit of a display device according to another embodiment of the present disclosure.

The embodiment of FIG. 20 differs from the embodiment of FIG. 18 in that a boost display pixel BPX is connected to a second voltage line VDL2, to which a second driving voltage is supplied.

The second driving voltage may be higher than a first driving voltage from a first voltage line VDL1, to which a normal display pixel NPX is connected. As a higher voltage is provided to the boost display pixel BPX than to the first normal display pixel NPX via a separate driving line, a higher driving current can be easily generated in the boost display pixel BPX than in the normal display pixel NPX, and as a result, a higher emission luminance can be obtained from the boost display pixel BPX than from the normal display pixel NPX.

Figure 21:
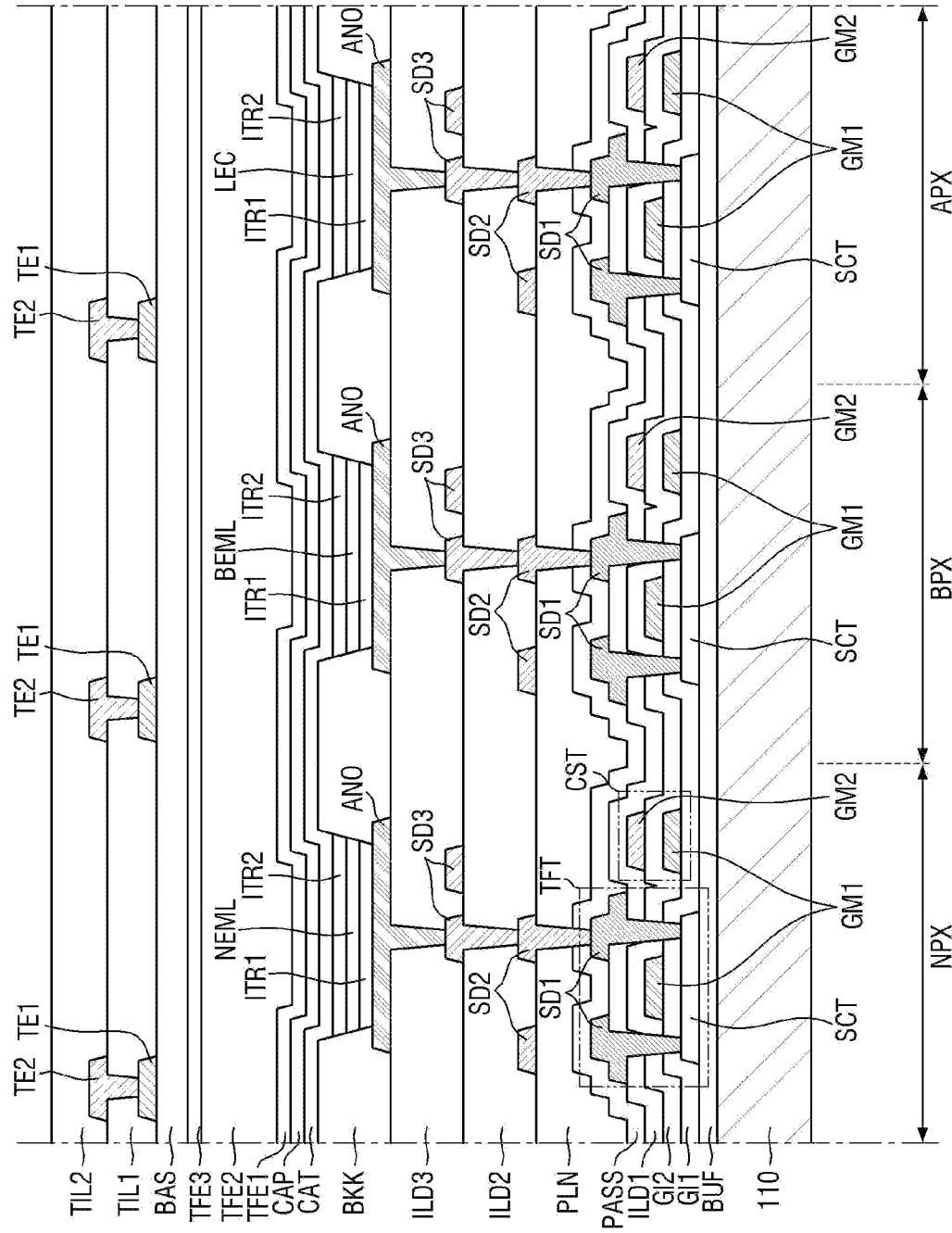
FIG. 21 is a cross-sectional view illustrating a normal display pixel, a boost display pixel and a light-receiving circuit of a display device according to an embodiment of the present disclosure.

FIG. 21 is a cross-sectional view illustrating a normal display pixel, a boost display pixel and a light-receiving circuit of a display device according to an embodiment of the present disclosure.

Referring to FIG. 21, a circuit layer is disposed on a substrate, a light-emitting layer and a light-receiving layer are disposed on the circuit layer, and a touch layer 130 (see FIG. 4 and FIG. 5) is disposed on the light-emitting layer and the light-receiving layer.

The circuit layer includes thin-film transistors (TFTs) "TFT", capacitors CST, and various lines. The TFTs TFT include gate electrodes, semiconductor layers SCT, source electrodes, and drain electrodes. The capacitors CST include first electrodes and second electrodes. The TFTs "TFT" and the capacitors CST of a normal display pixel NPX, a boost display pixel BPX, and a light-receiving pixel APX may be formed using the semiconductor layers SCT, a plurality of conductive layers (GM1, GM2, SD1, SD2, and SD3), and a plurality of insulating layers (BUF, GI1, GI2, ILD1, PSS, PLN, ILD2, and ILD3) that are all in the same layer.

The circuit layer includes the semiconductor layers SCT, which form the channels of the TFTs "TFT", and the conductive layers (GM1, GM2, SD1, SD2, and SD3) and the insulating layers (BUF, GI1, GI2, ILD1, PSS, PLN, ILD2, and ILD3), which form electrodes and lines.

For example, the gate electrodes of the TFTs "TFT" and the first electrodes of the capacitors CST may be formed of a first conductive layer GM1. For example, lines that provide various scan signals may be formed of a second conductive layer GM2. For example, the second electrodes of the capacitors CST may be formed of the second conductive layer GM2. For example, the source electrodes and the drain electrodes of the TFTs "TFT" may be formed of a third conductive layer SD1. The j-th and (j+1)-th data lines DLj and DLj+1, the first voltage line VDL1, the second voltage line VDL2, and the initialization voltage line VIL of any one of FIGS. 18, 19, and 20 may be formed of at least one of the third conductive layer SD1, a fourth conductive layer SD2, and a fifth conductive layer SD3. Connecting electrodes that connect the first electrodes of light-emitting elements or light-receiving elements to the drain electrodes of the TFTs "TFT" may be formed of at least one of the fourth and fifth conductive layers SD2 and SD3.

The first and second conductive layers GM1 and GM2 may be single films or multilayer films including at least one metal selected from among molybdenum (Mo), aluminum (Al), platinum (Pt), palladium (Pd), silver (Ag), magnesium (Mg), gold (Au), nickel (Ni), neodymium (Nd), iridium (Jr), chromium (Cr), calcium (Ca), titanium (Ti), tantalum (Ta), tungsten (W), and copper (Cu). The third, fourth, and fifth conductive layers SD1, SD2, and SD3 may include at least one metal selected from among Al, Mo, Pt, Pd, Ag, Mg, Au, Ni, Nd, Ir, Cr, Ca, Ti, Ta, W, and Cu and may be formed to have a stack structure such as Ti/Al/Ti, Mo/Al/Mo, Mo/AlGe/Mo, or Ti/Cu. The first and second conductive layers GM1 and GM2 may be formed of the same material, and the third, fourth, and fifth conductive layers SD1, SD2, and SD3 may be formed of the same material, but may include a different material from the first and second conductive layers GM1 and GM2. The number of conductive layers in the circuit layer is not particularly limited, but may vary.

The insulating films (BUF, GI1, GI2, ILD1, PSS, PLN, ILD2, and ILD3) may be interposed between the conductive layers (GM1, GM2, SD1, SD2, and SD3) and the semiconductor layers SCT. The insulating films (BUF, GI1, GI2, ILD1, PSS, PLN, ILD2, and ILD3) may include a buffer layer BUF, which covers a substrate 110 and is disposed between the substrate 110 and the semiconductor layers SCT, a first gate insulating film GI1, which is interposed between the semiconductor layers SCT and the first conductive layer GM1, a second gate insulating film GI2, which is interposed between the first conductive layer GM1 and the second conductive layer GM2, a first interlayer insulating film ILD1, which is disposed on the second conductive layer GM2, a passivation film PASS, which is disposed on the third conductive layer SD1, a planarization film PLN, which is disposed on the passivation film PASS, a second interlayer insulating film ILD2, which is disposed on the fourth conductive layer SD2, and a third interlayer insulating film ILD3, which is disposed on the fifth conductive layer SD3.

The insulating films (BUF, GI1, GI2, ILD1, PSS, PLN, ILD2, and ILD3) may be formed as inorganic films (such as SiN, SiO, or SiON films), as organic films, as organic/inorganic films, or as stacks of inorganic and organic films.

The light-emitting layer and the light-receiving layer are disposed on the circuit layer. Specifically, a light-emitting element of the normal display pixel NPX, a light-emitting element of the boost display pixel BPX, and a light-receiving element of the light-receiving pixel APX are disposed on the circuit layer.

The light-emitting element of the normal display pixel NPX includes a first electrode ANO, a second electrode CAT, and a normal light-emitting layer NEML, which is interposed between the first electrode ANO and the second electrode CAT. The normal light-emitting layer NEML may include an organic light-emitting material, but the present disclosure is not limited thereto. Alternatively, the normal light-emitting layer NEML may include an inorganic light-emitting material. A hole injection/transport layer ITR1 may be interposed between the first electrode ANO and the normal light-emitting layer NEML of the normal display pixel NPX, and an electron injection/transfer layer ITR2 may be interposed between the normal light-emitting layer NEML and the second electrode CAT of the normal display pixel NPX.

The light-emitting element of the boost display pixel BPX includes a first electrode ANO, a second electrode CAT, and a boost light-emitting layer BEML, which is interposed between the first electrode ANO and the second electrode CAT. The boost light-emitting layer BEML may include an organic light-emitting material, but the present disclosure is not limited thereto. Alternatively, the boost light-emitting layer BEML may include an inorganic light-emitting material. A hole injection/transport layer ITR1 may be interposed between the first electrode ANO and the boost light-emitting layer BEML of the boost display pixel BPX, and an electron injection/transfer layer ITR2 may be interposed between the boost light-emitting layer BEML and the second electrode CAT of the boost display pixel BPX.

The light-receiving element of the light-receiving pixel APX includes a first electrode ANO, a second electrode CAT, and a photoelectric conversion layer LEC, which is interposed between the first electrode ANO and the second electrode CAT. The photoelectric conversion layer LEC may include an organic photoelectric conversion material, but the present disclosure is not limited thereto. Alternatively, the photoelectric conversion layer LEC may include an inorganic photoelectric conversion material. A hole injection/transport layer ITR1 may be interposed between the first electrode ANO and the photoelectric conversion layer LEC of the light-receiving pixel APX, and an electron injection/transfer layer ITR2 may be interposed between the photoelectric conversion layer LEC and the second electrode CAT of the light-receiving pixel APX.

The first electrode ANO of the light-emitting element of the normal display pixel NPX, the first electrode ANO of the light-emitting element of the boost display pixel BPX, and the first electrode ANO of the light-receiving element of the light-receiving pixel APX may be disposed in the same layer. The first electrode ANO of the light-emitting element of the normal display pixel NPX, the first electrode ANO of the light-emitting element of the boost display pixel BPX, and the first electrode ANO of the light-receiving element of the light-receiving pixel APX may be formed of the same material on the third interlayer insulating film ILD3. A bank layer BNK is disposed on the first electrodes ANO. A plurality of openings, which expose the first electrodes ANO, is defined in the bank layer BNK, and active layers such as the normal light-emitting layer NEML, the boost light-emitting layer BEML, and the photoelectric conversion layer LEC are disposed on the first electrodes ANO exposed by the openings. The second electrode CAT of the light-emitting element of the normal display pixel NPX, the second electrode CAT of the light-emitting element of the boost display pixel BPX, and the second electrode CAT of the light-receiving element of the light-receiving pixel APX may be shared as an integral common electrode. The hole injection/transport layer ITR1 of the light-emitting element of the normal display pixel NPX, the hole injection/transport layer ITR1 of the light-emitting element of the boost display pixel BPX, and the hole injection/transport layer ITR1 of the light-receiving element of the light-receiving pixel APX may be formed of the same material on the same layer and may be fabricated at the same time by the same process, and the electron injection/transport layer ITR2 of the light-emitting element of the normal display pixel NPX, the electron injection/transport layer ITR2 of the light-emitting element of the boost display pixel BPX, and the electron injection/transport layer ITR2 of the light-receiving element of the light-receiving pixel APX may be formed of the same material on the same layer and may be fabricated at the same time by the same process. As the hole injection/transport layer ITR1 of the light-emitting element of the normal display pixel NPX, the hole injection/transport layer ITR1 of the light-emitting element of the boost display pixel BPX, and the hole injection/transport layer ITR1 of the light-receiving element of the light-receiving pixel APX share the same material, the hole injection/transport layer ITR1 of the light-emitting element of the normal display pixel NPX, the hole injection/transport layer ITR1 of the light-emitting element of the boost display pixel BPX, and the hole injection/transport layer ITR1 of the light-receiving element of the light-receiving pixel APX can be formed at the same time by a single process. Similarly, as the electron injection/transport layer ITR2 of the light-emitting element of the normal display pixel NPX, the electron injection/transport layer ITR2 of the light-emitting element of the boost display pixel BPX, and the electron injection/transport layer ITR2 of the light-receiving element of the light-receiving pixel APX share the same material, the electron injection/transport layer ITR2 of the light-emitting element of the normal display pixel NPX, the electron injection/transport layer ITR2 of the light-emitting element of the boost display pixel BPX, and the electron injection/transport layer ITR2 of the light-receiving element of the light-receiving pixel APX can be formed at the same time by a single process. Therefore, process efficiency can be improved.

A capping film CAP may be disposed on the second electrode CAT of the light-emitting element of the normal display pixel NPX, the second electrode CAT of the light-emitting element of the boost display pixel BPX, and the second electrode CAT of the light-receiving element of the light-receiving pixel APX, and a plurality of thin-film encapsulation layers (TFE1, TFE2, and TFE3) may be disposed on the capping film CAP. The thin-film encapsulation layers (TFE1, TFE2, and TFE3) may include a first encapsulation film TFE1, which is formed as an inorganic film such as a SiN, SiO, or SiON film, a second encapsulation film TFE2, which is disposed on the first encapsulation film TFE1 and includes an organic film, and a third encapsulation film TFE3, which is disposed on the second encapsulation film TFE2 and is formed as an inorganic film such as a SiN, SiO, or SiON film.

A touch layer 130 may include a base layer BAS, first touch conductive layers TE1, which are disposed on the base layer BAS, a first touch insulating film TILL which is disposed on the first touch conductive layers TE1, second touch conductive layers TE2, which are disposed on the first touch insulating film TIL1 and a second touch insulating film TIL2, which covers the second touch conductive layers TE2. The touch layer 130 is disposed on the thin-film encapsulation layers (TFE1, TFE2, and TFE3).

The boost display pixel BPX is disposed adjacent to the light-receiving pixel APX. The arrangement of the boost display pixel BPX may be dependent upon the arrangement of the light-receiving pixel APX. Various layouts of boost display pixel areas BPXR and light-receiving pixel areas APXR will hereinafter be described.

Figure 22:
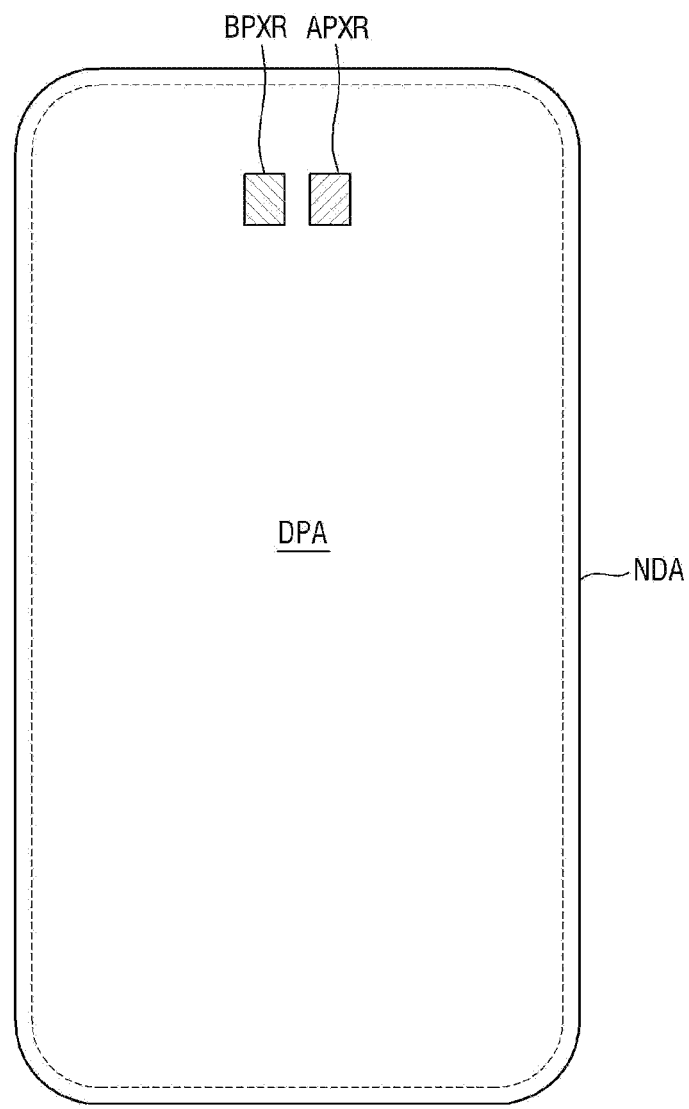
FIG. 22 is a plan view of a display device according to an embodiment of the present disclosure.

FIG. 22 is a plan view of a display device according to an embodiment of the present disclosure.

Referring to FIG. 22, a boost display pixel area BPXR is disposed in part of a display area DPA, and a light-receiving pixel area APXR is disposed on one side (e.g., on the right side) of the boost display pixel area BPXR. The boost display pixel area BPXR and the light-receiving pixel area APXR may have a rectangular or bar shape.

The light-receiving pixel area APXR may include one or more light-receiving pixels APX. The light-receiving pixel area APXR may further include normal display pixels NPX.

The boost display pixel area BPXR may include one or more boost display pixels BPX. The boost display pixel area BPXR may consist only of the boost display pixels BPX, but the present disclosure is not limited thereto. Alternatively, the boost display pixel area BPXR may include not only the boost display pixels BPX, but also normal display pixels NPX. In a case where the boost display pixels BPX and the normal display pixels NPX coexist in the boost display pixel area BPXR, the boost display pixels BPX may display a particular color and may thus replace normal display pixels NPX corresponding to the particular color. For example, in a case where the boost display pixels BPX are red boost display pixels BPX, green normal display pixels NPX and blue normal display pixels NPX may be provided in the boost display pixel area BPXR, but no red normal display pixels NPX may be disposed in the boost display pixel area BPXR. However, the present disclosure is not limited to this. Alternatively, normal display pixels NPX that display the same color as the boost display pixels BPX may also be provided in the boost display pixel area BPXR.

In a case where the boost display pixel area BPXR is disposed adjacent to the light-receiving pixel area APXR, as illustrated in FIG. 22, light emitted from the boost display pixels BPX is highly likely to be incident upon the light-receiving pixels APX, and as a result, the efficiency of light reception can be improved.

Figure 23:
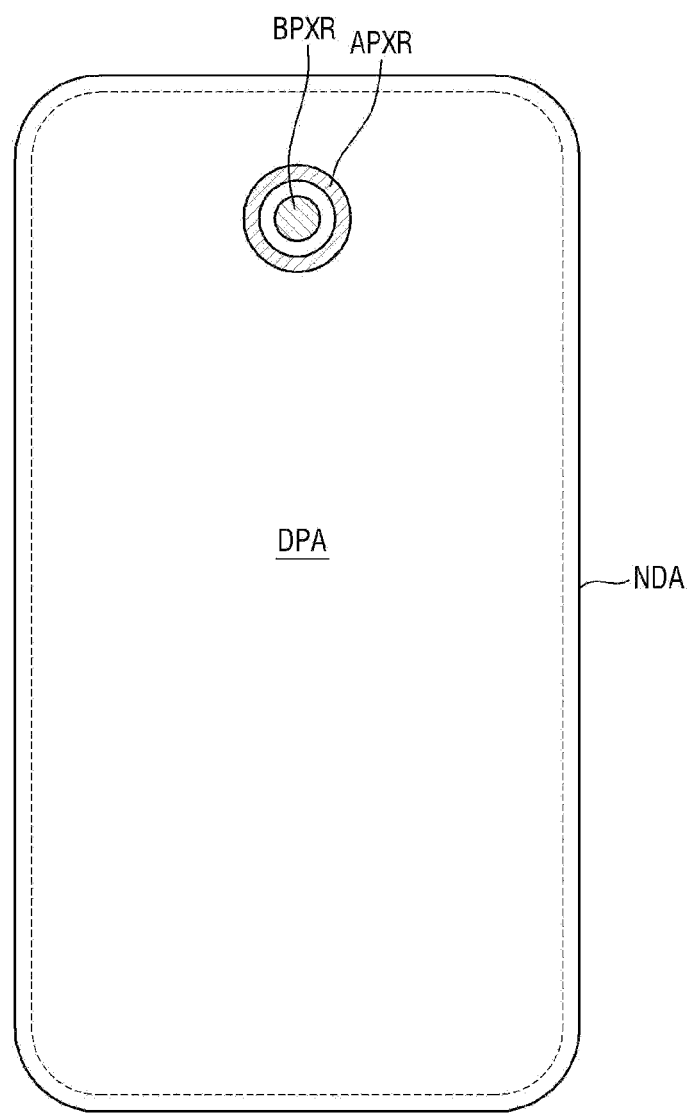
FIG. 23 is a plan view of a display device according to another embodiment of the present disclosure.

FIG. 23 is a plan view of a display device according to another embodiment of the present disclosure.

The embodiment of FIG. 23 differs from the embodiment of FIG. 22 in that a light-receiving pixel area APXR is disposed to surround a boost display pixel area BPXR. Referring to FIG. 23, the boost display pixel area BPXR may have a circular shape in a plan view, and the light-receiving pixel area APXR may have a donut shape in a plan view to surround the boost display pixel area BPXR. In the embodiment of FIG. 23, as light emitted from the boost display pixels BPX is highly likely to be incident upon the light-receiving pixels APX, an excellent light reception efficiency can be provided.

Alternatively, the boost display pixel area BPXR may be disposed to surround the light-receiving pixel area APXR.

Figure 24:
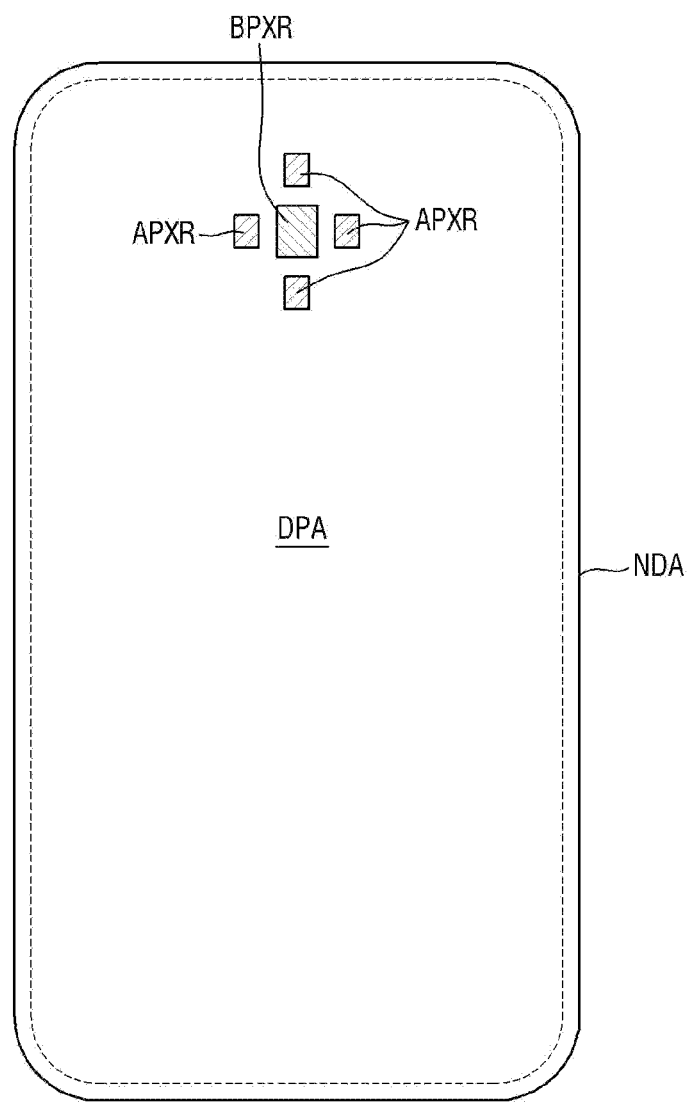
FIG. 24 is a plan view of a display device according to another embodiment of the present disclosure.

FIG. 24 is a plan view of a display device according to another embodiment of the present disclosure.

The embodiment of FIG. 24 differs from the embodiment of FIG. 22 in that a plurality of light-receiving pixel areas APXR are provided and are disposed on four sides (e.g., on the left, right, upper, and lower sides) of a boost display pixel area BPXR. Referring to FIG. 24, as the light-receiving pixel areas APXR are disposed adjacent to all the four sides of the boost display pixel area BPXR, an excellent light reception efficiency can be provided.

Figure 25:
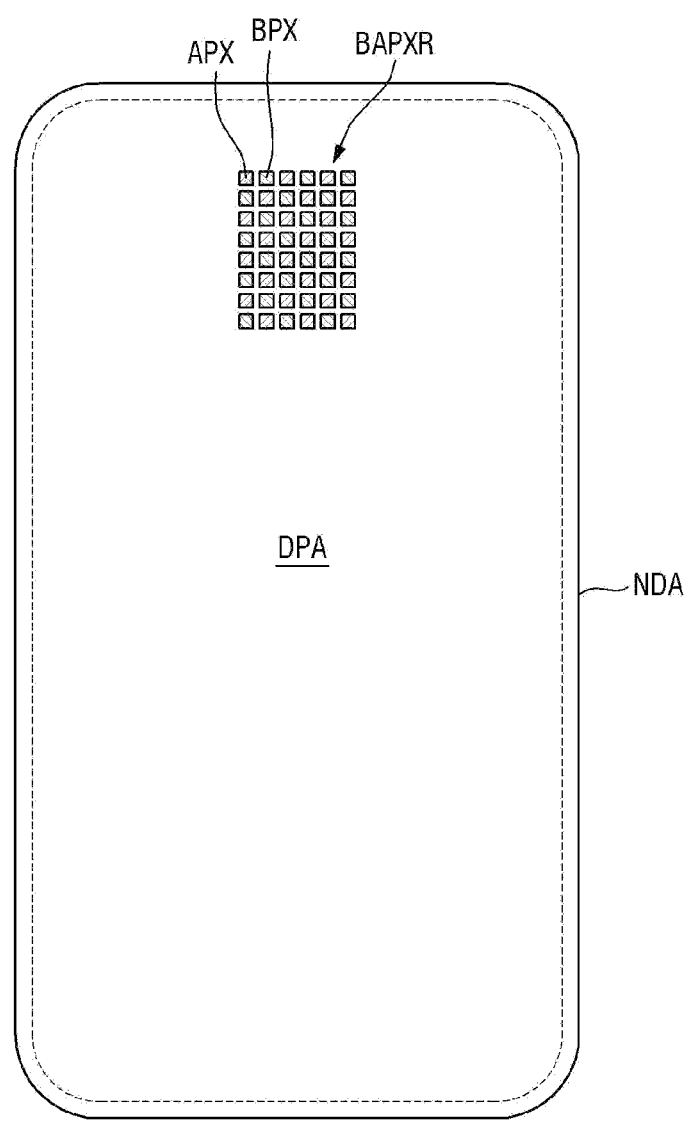
FIG. 25 is a plan view of a display device according to another embodiment of the present disclosure.

FIG. 25 is a plan view of a display device according to another embodiment of the present disclosure.

The embodiment of FIG. 25 differs from the embodiments of FIGS. 22, 23, and 24 in that a boost display pixel/light-receiving pixel area BAPXR is disposed in part of a display area DPA. Referring to FIG. 25, boost display pixels BPX and light-receiving pixels APX are alternately arranged in the boost display pixel/light-receiving pixel area BAPXR to be adjacent to one another. Although not specifically illustrated, normal display pixels NPX may be further disposed in the boost display pixel/light-receiving pixel area BAPXR, in which case, the normal display pixels NPX, the boost display pixels BPX, and the light-receiving pixels APX may be alternately arranged.

As the boost display pixels BPX and the light-receiving pixels APX are alternately arranged to be adjacent to one another, the distance between the boost display pixels BPX and the light-receiving pixels APX can be minimized. Accordingly, an excellent light reception efficiency can be provided.

Figure 26:
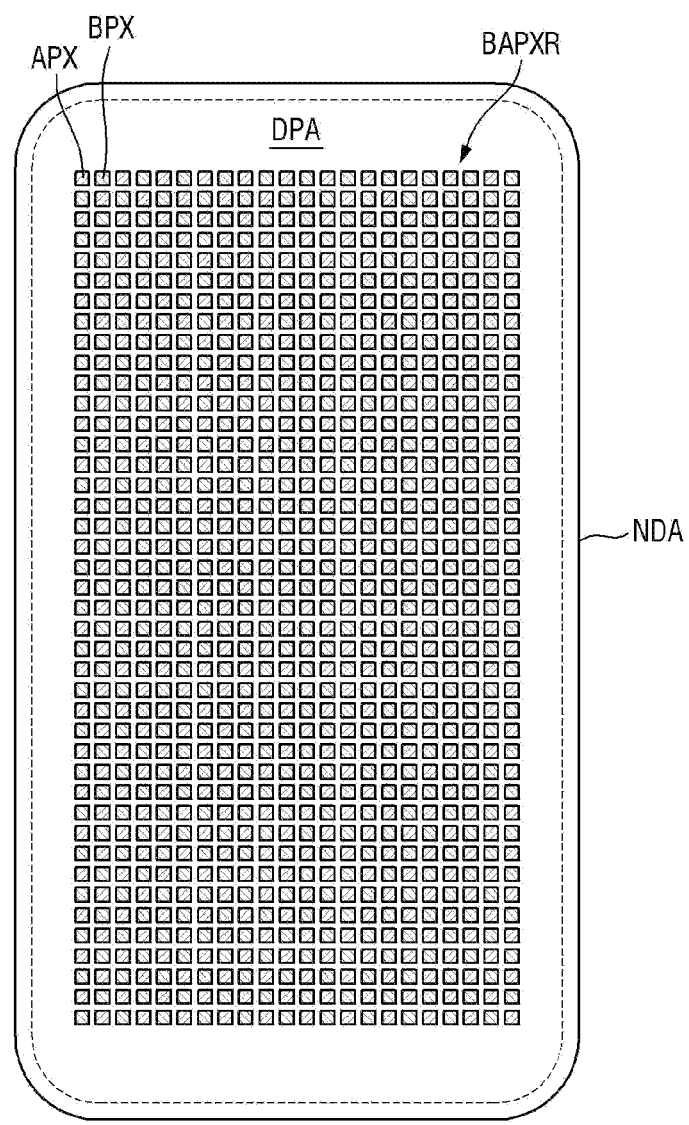
FIG. 26 is a plan view of a display device according to another embodiment of the present disclosure.

FIG. 26 is a plan view of a display device according to another embodiment of the present disclosure.

The embodiment of FIG. 26 differs from the embodiment of FIG. 25 in that a boost display pixel/light-receiving pixel area BAPXR is formed to account for most of a display area DPA (e.g., at least 80% of the display area DPA). Although not shown herein, normal display pixels NPX may also be disposed in the boost display pixel/light-receiving pixel area BAPXR so that a normal display operation may also be performed.

As boost display pixels BPX and light-receiving pixels APX are alternately arranged to be adjacent to one another, an excellent light reception efficiency can be provided. Also, as a wide boost display pixel/light-receiving pixel area BAPXR is provided, blood pressure measurement can be further facilitated.

In a display device according to the embodiments, a blood pressure measurement module can be incorporated into a display device without the addition of any complicated structure. Also, as boost display pixels with a higher maximum luminance than normal display pixels are provided, the signal-to-noise ratio (SNR) of light-receiving elements can be improved.

While the present disclosure has been particularly shown and described with reference to embodiments thereof, it will be understood by those of ordinary skill in the art that various changes in form and detail may be made therein without departing from the spirit and scope of the present disclosure as defined by the following claims. The embodiments of the present disclosure described herein should be considered in a descriptive sense only and not for purposes of limitation.

What is claimed is:

1. A display device comprising:
a plurality of normal display pixels;
at least one boost display pixel having a higher maximum luminance than the plurality of normal display pixels with respect to a same maximum effective current; and
at least one light-receiving pixel disposed adjacent to the at least one boost display pixel,
wherein
each of the plurality of normal display pixels, the at least one boost display pixel, and the at least one light-receiving pixel includes a first electrode, a second electrode, and an active layer which is interposed between the first and second electrodes,
the first electrode of each of the plurality of normal display pixels, the first electrode of the at least one boost display pixel, and the first electrode of the at least one light-receiving pixel are disposed in a same layer, and
the second electrode of each of the plurality of normal display pixels, the second electrode of the at least one boost display pixel, and the second electrode of the at least one light-receiving pixel are integrally connected to one another.

2. The display device of claim 1, wherein a maximum luminance of the at least one boost display pixel is 1.5 times or greater than a maximum luminance of the plurality of normal display pixels.

3. The display device of claim 1, wherein
the plurality of normal display pixels includes red normal display pixels emitting red light, green normal display pixels emitting green light, and blue normal display pixels emitting blue light, and
the at least one boost display pixel emits light of a green wavelength or longer.

4. The display device of claim 3, wherein
the red normal display pixels, the green normal display pixels, and the blue normal display pixels are alternately arranged in row and column directions, and
the at least one boost display pixel emits red light or green light and replaces at least one normal display pixel that emits light of a same color as the at least one boost display pixel.

5. The display device of claim 3, wherein the at least one boost display pixel emits red light or green light.

6. The display device of claim 5, wherein the at least one boost display pixel has a larger emission area than the at least one normal display pixel emitting light of a same color as the at least one boost display pixel.

7. The display device of claim 5, wherein a light-emitting layer of the at least one boost display pixel is thicker than a light-emitting layer of the at least one normal display pixel emitting light of a same color as the at least one boost display pixel.

8. The display device of claim 5, wherein
a light-emitting layer of the at least one boost display pixel includes a first light-emitting material,
the at least one normal display pixel emitting light of a same color as the at least one boost display pixel includes a second light-emitting material, and
the first light-emitting material has a higher emission efficiency than the second light-emitting material.

9. The display device of claim 8, wherein the second light-emitting material has a higher color reproducibility than the first light-emitting material.

10. The display device of claim 1, further comprising:
a normal display pixel circuitry for driving the plurality of normal display pixels; and
a boost display pixel circuitry for driving the at least one boost display pixel,
wherein the normal pixel circuitry includes more transistors than the boost display pixel circuitry.

11. A display device comprising:
a substrate including a display area having a plurality of pixels;
a plurality of first electrodes disposed in the pixels, on the substrate;
a second electrode facing the first electrodes; and
a plurality of active layers disposed in the pixels, between the first electrodes and the second electrode,
wherein
some of the pixels include normal display light-emitting layers as the active layers,
some of the pixels include boost display light-emitting layers which have higher emission luminance than the normal display light-emitting layers with respect to a same maximum effective current as the active layers, and
some of the pixels include photoelectric conversion layers as the active layers.

12. The display device of claim 11, wherein a maximum luminance of the boost display light-emitting layers is 1.5 times or greater than a maximum luminance of the normal display light-emitting layers.

13. The display device of claim 11, wherein
the display area includes a boost display pixel area where the pixels including the boost display light-emitting layers are disposed and a light-receiving pixel area where the pixels including the photoelectric conversion layers are disposed, and
the boost display pixel area and the light-receiving pixel area are disposed adjacent to each other.

14. The display device of claim 13, wherein the light-receiving pixel area surrounds the boost display pixel area in a plan view.

15. The display device of claim 13, wherein the display area includes a boost display pixel/light-receiving pixel area where the pixels including the boost display light-emitting layers and the pixels including the photoelectric conversion layers are alternately arranged to be adjacent to one another.

16. The display device of claim 11, further comprising:
a pressure sensing member disposed on a bottom surface of the substrate or on a top surface of the second electrode.

17. A display device comprising:
a display unit including a plurality of normal display pixels, at least one boost display pixel which has a higher maximum luminance than the plurality of normal display pixels with respect a same maximum effective current, and at least one light-receiving pixel;
a sensor unit including a pressure sensor; and
a control unit,
wherein the control unit includes an emission driving module configured to control the plurality of normal display pixels and the at least one boost display pixel to emit light or not to emit light and control the amount by which the plurality of normal display pixels and the at least one boost display pixel are to emit light, a light reception data determination module configured to receive an electrical signal from the at least one light-receiving pixel and determine light reception data based on the received electrical signal, a pulse wave signal generation module configured to generate a pulse wave signal based on the light reception data, a pressure data determination module configured to receive an electrical signal from the pressure sensor and determine pressure data based on the received electrical signal, and a blood pressure measurement module configured to measure blood pressure based on the pulse wave signal and the pressure data.

18. The display device of claim 17, wherein, in a blood pressure measurement mode, the emission driving module controls the at least one boost display pixel to emit light at a maximum luminance.

19. The display device of claim 18, wherein, in a normal display mode, the emission driving module controls an amount of light to be emitted by the plurality of normal display pixels based on a gray level of the plurality of normal display pixels.

20. The display device of claim 19, wherein, in the normal display mode, the emission driving module controls an amount of light to be emitted by the at least one boost display pixel in accordance with gray data corresponding to a location of the at least one boost display pixel.

* * * * *